United States Patent
Haas et al.

(10) Patent No.: US 6,391,303 B1
(45) Date of Patent: May 21, 2002

(54) METHODS AND COMPOSITIONS FOR INDUCING ORAL TOLERANCE IN MAMMALS

(75) Inventors: Susan Haas, Monsey; Sam J. Milstein, Larchmont, both of NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 09/101,921

(22) PCT Filed: Aug. 20, 1997

(86) PCT No.: PCT/US97/14676

§ 371 Date: May 3, 1999

§ 102(e) Date: May 3, 1999

(87) PCT Pub. No.: WO98/21951

PCT Pub. Date: May 28, 1998

Related U.S. Application Data

(60) Provisional application No. 60/031,356, filed on Nov. 18, 1996, and provisional application No. 60/049,691, filed on Jun. 16, 1997.

(51) Int. Cl.$^7$ .............................................. A61K 39/00
(52) U.S. Cl. .............................. 424/185.1; 424/183.1; 514/54; 514/617
(58) Field of Search ................ 514/54, 617; 424/183.1

(56) References Cited

U.S. PATENT DOCUMENTS

| | | | |
|---|---|---|---|
| 4,061,466 A | 12/1977 | Sjoholm et al. ............. 424/311 |
| 4,147,767 A | 4/1979 | Yapel ........................... 424/22 |
| 4,238,506 A | 12/1980 | Heerdt et al. ................ 424/319 |
| 4,239,754 A | 12/1980 | Sache et al. ................ 424/183 |
| 4,442,090 A | 4/1984 | Kakeya et al. ............. 424/178 |
| 4,462,991 A | 7/1984 | Higuchi et al. ............. 424/177 |
| 4,656,161 A | 4/1987 | Dieter .......................... 514/56 |
| 4,692,433 A | 9/1987 | Hostetler .................... 514/12 |
| 4,703,042 A | 10/1987 | Bodor .......................... 514/56 |
| 4,757,066 A | 7/1988 | Shiokari et al. ............ 514/210 |
| 4,873,087 A | 10/1989 | Morishita et al. .......... 424/433 |
| 4,886,663 A | 12/1989 | Houghten .................... 424/88 |
| 4,895,725 A | 1/1990 | Kantor et al. .............. 424/455 |
| 4,900,730 A | 2/1990 | Miyauchi .................... 514/12 |
| 4,925,673 A | 5/1990 | Steiner et al. .............. 424/455 |
| 4,976,968 A | 12/1990 | Steiner ........................ 424/491 |
| 4,983,402 A | 1/1991 | Steiner ........................ 424/491 |
| 5,122,367 A | 6/1992 | Ron et al. ..................... 424/80 |
| 5,271,961 A | 12/1993 | Mathiowitz et al. ... 427/213.31 |
| 5,352,461 A | 10/1994 | Feldstein et al. ........... 424/493 |
| 5,389,379 A | 2/1995 | Dirix et al. ................. 424/451 |
| 5,401,516 A | 3/1995 | Milstein et al. ............ 424/491 |
| 5,443,841 A | 8/1995 | Milstein et al. ............ 424/451 |
| 5,447,728 A | 9/1995 | Milstein et al. ............ 424/490 |
| 5,451,410 A | 9/1995 | Milstein et al. ............ 424/490 |
| 5,540,939 A | 7/1996 | Milstein et al. ............ 424/491 |
| 5,541,155 A | 7/1996 | Leone-Bay et al. ........... 514/2 |
| 5,578,323 A | 11/1996 | Milstein et al. ............ 424/499 |
| 5,601,846 A | 2/1997 | Milstein et al. ............ 424/499 |
| 5,629,020 A | 5/1997 | Leone-Bay et al. ......... 424/489 |
| 5,643,957 A | 7/1997 | Leone-Bay et al. ......... 514/563 |
| 5,650,386 A | 7/1997 | Leone-Bay et al. ........... 514/2 |
| 5,667,806 A | 9/1997 | Kantor ........................ 424/484 |
| 5,693,338 A | 12/1997 | Milstein .................... 424/451 |
| 5,709,861 A | 1/1998 | Santiago et al. .......... 424/184.1 |
| 5,714,167 A | 2/1998 | Milstein et al. ............. 424/490 |
| 5,750,147 A | 5/1998 | Kantor ........................ 424/491 |
| 5,766,633 A | 6/1998 | Milstein et al. ............. 424/489 |
| 5,773,647 A | 6/1998 | Leone-Bay et al. ......... 562/444 |
| RE35,862 E | 7/1998 | Steiner et al. .............. 424/455 |
| 5,776,888 A | 7/1998 | Leone-Bay et al. ........... 514/2 |
| 5,792,451 A | 8/1998 | Sarubbi et al. ............. 424/85.4 |
| 5,804,688 A | 9/1998 | Leone-Bay et al. ......... 562/444 |
| 5,811,127 A | 9/1998 | Milstein et al. ............. 424/490 |
| 5,820,881 A | 10/1998 | Milstein .................... 424/489 |
| 5,824,345 A | 10/1998 | Milstein .................... 424/489 |
| 5,840,340 A | 11/1998 | Milstein et al. ............. 424/499 |
| 5,863,944 A | 1/1999 | Leone-Bay et al. ......... 514/559 |
| 5,866,536 A | 2/1999 | Leone-Bay et al. ........... 514/2 |
| 5,876,710 A | 3/1999 | Leone-Bay et al. ........ 424/85.1 |
| 5,879,681 A | 3/1999 | Leone-Bay et al. ........ 424/85.1 |
| 5,935,601 A | 8/1999 | Leone-Bay et al. ......... 424/489 |
| 5,939,381 A | 8/1999 | Leone-Bay et al. ........... 514/2 |
| 5,955,503 A | 9/1999 | Leone-Bay et al. ......... 514/563 |
| 5,958,457 A | 9/1999 | Santiago et al. ............. 424/490 |
| 5,962,710 A | 10/1999 | Gschneidner et al. ....... 554/112 |
| 5,965,121 A | 10/1999 | Leone-Bay et al. ........ 424/85.2 |
| 5,972,387 A | 10/1999 | Milstein et al. ............. 424/491 |
| 5,976,569 A | 11/1999 | Milstein .................... 424/451 |
| 5,989,539 A | 11/1999 | Leone-Bay et al. ........ 424/85.2 |
| 5,990,166 A | 11/1999 | Leone-Bay et al. ......... 514/563 |
| 6,001,347 A | 12/1999 | Leone-Bay et al. ........ 424/85.1 |
| 6,051,258 A | 4/2000 | Kantor ........................ 424/491 |

(List continued on next page.)

FOREIGN PATENT DOCUMENTS

| | | |
|---|---|---|
| EP | 0036145 | 9/1981 |
| EP | 226223 | 6/1987 |
| EP | 0517211 | 9/1992 |
| GB | 2095994 | 10/1982 |
| WO | 8807378 | 10/1988 |
| WO | 9219263 | 11/1992 |
| WO | WO 96/21458 A1 * | 7/1996 |

OTHER PUBLICATIONS

Picciola G.: "Sintesi Di Acidi Chiazolinioici E Benzossazinonici E Studio Delle Loro Proprieta Antiniammatorie" IT, Societa Chimica Italiana Pavia vol. 31, No. 9, pp. 655–664 and English Translation.

*Primary Examiner*—Dwayne C. Jones
(74) *Attorney, Agent, or Firm*—Davidson, Davidson & Kappel, LLC

(57) ABSTRACT

The present invention relates to methods and pharmaceutical formulations for orally delivering an antigen to induce tolerance. The antigen is combined with derivatized amino acids or salts thereof. The induction of oral tolerance may be applied clinically for the prevention or treatment of autoimmune diseases and clinical allergic hypersensitivities, and for the prevention of allograft rejection.

27 Claims, 12 Drawing Sheets

U.S. PATENT DOCUMENTS

| | | |
|---|---|---|
| 6,051,561 A | 4/2000 | Leone-Bay et al. ............ 514/56 |
| 6,060,513 A | 5/2000 | Leone-Bay et al. .......... 514/559 |
| 6,071,510 A | 6/2000 | Leone-Bay et al. ........ 424/85.2 |
| 6,071,538 A | 6/2000 | Milstein et al. ............. 424/464 |
| 6,084,112 A | 7/2000 | Ho et al. .................... 554/114 |
| 6,090,958 A | 7/2000 | Leone-Bay et al. ......... 554/112 |
| 6,099,856 A | 8/2000 | Milstein et al. ............. 424/450 |
| 6,100,285 A | 8/2000 | Kantor ....................... 514/400 |
| 6,100,298 A | 8/2000 | Leone-Bay et al. ......... 514/563 |
| 6,180,140 B1 | 1/2001 | Leone-Bay et al. ......... 424/489 |

* cited by examiner

US 6,391,303 B1

METHODS AND COMPOSITIONS FOR INDUCING ORAL TOLERANCE IN MAMMALS

CROSS-REFERENCES TO RELATED APPLICATIONS

The present application is based upon two U.S. Provisional Patent Applications: serial No. 60/031,356 filed on Nov. 18, 1996 and serial No. 60/049,691 filed on Jun. 16, 1997. Applicant claims the benefits of the filing dates of the aforesaid provisional applications under 35 U.S.C. §119.

FIELD OF THE INVENTION

The present invention relates to methods and compositions useful for the induction of oral tolerance to a coadministered antigen in mammals.

BACKGROUND OF THE INVENTION

Immunological antibody responses to pathogens are required to prevent infections in the body, whereas, immunological tolerance is a property of the immune system that allows for the discrimination of self from non-self. A breakdown in immunological tolerance to self antigens allows the onset of anti-self immunological responses through the generation of anti-self antibodies and/or cellular immune responses. This breakdown is responsible for auto-immune diseases seen in both humans and other mammals.

Allergic immune responses to allergens such as those classically observed in, for example, hay fever, reactions to insect bites and common food allergies is suppressed through the generation of immunological tolerance to the antigen responsible for the allergy, i.e., the allergen. Repeated exposure to a particular allergen through controlled administration of allergen can induce tolerance in some patients.

Oral tolerance has been characterized in the literature as a state of antigen-specific systemic immunological unresponsiveness or tolerance, which is induced by prior oral administration or feeding of antigen. (A. M. Mowat, *Immunology Today*, Vol. 8, No. 3, 1987, pp. 93–98.) Such a state of systemic hyporesponsiveness to an administered protein or antigen has been observed and reviewed in the art. (H. L. Weiner, *Proc. Natl. Acad. Sci. USA*, Vol. 91, 1994, pp. 10762–10765; and H. L. Weiner and L. F. Mayer, eds., *Annals of NY Acad. Sci.*, Vol. 778, 1996, pp. xiii–xviii.)

It has been shown that oral co-administration of antigens with cholera toxin B subunit as a delivery agent provides an efficient transmucosal delivery system for induction of immunological tolerance. (J. B. Sun, et al., *Proc. Natl. Acad. Sci. USA*, Vol. 91, 1994, pp. 10795–10799; and C. Czerkinsky, et al., *Annals NY Acad. Sci.*, Vol. 778, 1996, pp. 185–193.) In these studies sheep red blood cells (SRBC), horse red blood cells (HRBC) or purified human gammaglobulin (HGG) were used as antigen and covalently conjugated to the cholera toxin B (CTB) subunit delivery agent. The SRBC-CTB, HRBC-CTB or HGG-CTB were administered orally to mice to induce oral tolerance to these antigens.

One example of a inflammatory demyelinating autoimmune disease in humans is Multiple Sclerosis. Experimental Autoimmune (a.k.a. Allergic) Encephalomyelitis (EAE) is a paralytic disease of the central nervous system (CNS) that can be induced in animals by injection, together with Complete Freund's Adjuvant, of brain or spinal cord homogenate, purified Myelin Basic Protein (MBP) or other purified encephalitogenic proteins (derived from brain or spinal cord) or synthetic peptides whose amino acid sequences resemble those of encephalitogenic components of CNS tissues. EAE is widely used as a model for human autoimmune inflammatory demyelinating disorders such as Multiple Sclerosis (J-B. Sun, et al, Proc. Nat'l Acad. Sci., USA, 93, 7196–7201 (1996)). Certain strains of animals display greater susceptibility to the disease, including Lewis rats and SJL/J mice. Cats, dogs, Guinea Pigs and rabbits may also be susceptible. The most common source of active encephalitogens is Guinea Pig brain or spinal cord.

The encephalitogen/adjuvant suspension is injected into the footpads of experimental animals, inducing the onset of disease symptoms within 10–12 days. Prevention or modulation of EAE symptoms has been achieved by induction of oral tolerance via oral administration of large, numerous doses of MBP either before or after induction of the disease. Generally, at least five oral doses are required. Determination of synergistic or immune enhancing agents to be administered together with MBP in order to reduce the number or magnitude of the MBP doses required to modulate the disease symptoms is desirable. If such agents could be identified, immunogenic tolerance to these and other types of autoimmune diseases could be promoted.

SUMMARY OF THE INVENTION

The present invention relates to methods and formulations for inducing oral tolerance in a mammal, comprising orally administering to the mammal a pharmaceutical formulation comprising an antigen and a delivery agent or agents comprising at least one derivatized amino acid or a salt thereof in an amount sufficient to induce oral tolerance. These delivery agents allow the administration of lower or fewer doses of antigen than are required to induce the same degree of systemic immune suppression with the antigen alone. The immune responses involved include, but are not limited to, systemic antibody production or delayed-type hypersensitivity reactions. In addition, the antigens for use in the induction of oral tolerance do not have to be covalently linked to the delivery agents.

It is believed that the foregoing delivery agents, when used in the proportions noted below, enhance the action of the antigens by increasing the proportion of ingested antigen which reaches the systemic circulation in its tolerogenic form. It may be that this is achieved by stabilization by the delivery agent of the tolerogenic form or fraction of the antigen in a configuration which may more easily cross the mucosal epithelium. It will be understood that the methods and compositions of the invention are not limited by the foregoing possible mode of action.

The invention relates to methods of inducing oral tolerance in a mammal wherein the derivatized amino acid is comprised of an amino acid bearing a free carboxyl group, an amide linkage and a hydrophobic chain comprised of aromatic and/or aliphatic components.

A preferred embodiment of the invention relates to methods of inducing oral tolerance in a mammal wherein the derivatized amino acid is an acylated amino acid compound of the formula $$Ar-\overset{O}{\underset{\|}{C}}-(R^4)-OH \qquad I$$

Ar is a substituted or unsubstituted phenyl,

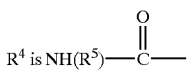

R⁵ is $C_1$ to $C_{10}$ alkyl, $C_1$ to $C_{10}$ alkenyl, phenyl, naphthyl, ($C_1$ to $C_{10}$ alkyl)phenyl, ($C_1$ to $C_{10}$ alkenyl)phenyl, ($C_1$ to $C_{10}$ alkyl)naphthyl, ($C_1$ to $C_{10}$ alkenyl)naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

R⁵ is optionally substituted with $C_1$ to $C_4$ alkyl, $C_1$ to $C_4$ alkenyl, $C_1$ to $C_4$ alkoxy, —OH, —SH and —$CO_2R^6$, cycloalkyl, cycloalkenyl, heteroalkyl, alkaryl, heteroaryl, heteroalkaryl, or any combination thereof; and R⁶ is hydrogen, $C_1$ to $C_4$ alkyl or $C_1$ to $C_4$ alkenyl.

Another preferred embodiment of the invention relates to methods of inducing oral tolerance in a mammal wherein the derivatized amino acid is a sulphonated amino acid compound of the formula

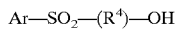

Ar—$SO_2$—($R^4$)—OH        II wherein Ar and R⁴ are as defined above.

Examples of the aforementioned derivatized amino acids are described in FIG. 1 below and include:

4-[4-(N-salicyloyl)]aminophenyl butyric acid (E352);

N-salicyloyl phenylalanine (E94);

4-[4-(N-benzenesulfonyl)]aminophenyl butyric acid (E198);

3-[4-(N-2,3-dimethoxybenzoyl)]aminophenyl propionic acid (E702);

10-(N-salicyloyl)amino decanoic acid (E597);

4-[4-(N-4 phenylbutyryl)]aminophenyl butyric acid (E445);

4-[4-(N-2 methoxybenzoyl)]aminophenyl butyric acid (E579);

3-[4-(N-2 methoxybenzoyl)]aminophenyl propionic acid (E594); and

4-[4-(N-phenoxyacetyl)]aminophenyl butyric acid (E623).

The present invention also relates to pharmaceutical formulations for inducing oral tolerance in a mammal, comprising an antigen and a delivery agent or agents comprising at least one derivatized amino acid or a salt thereof in an amount sufficient to induce oral tolerance. Preferably, the invention relates to pharmaceutical formulations for inducing oral tolerance, wherein the derivatized amino acid is administered at a dose of about 100–1000 mg per kg of the subject's body weight, preferably at a dose of about 250–750 mg per kg of body weight.

Also contemplated are methods and pharmaceutical preparations incorporating an adjuvant or adjuvants with the antigen and delivery agent or agents. The formulations are particularly advantageous for inducing oral tolerance to antigens which otherwise would require large and/or chronic dosing of antigen to induce such tolerance and which, by themselves, do not pass or are not taken up in the gastrointestinal mucosa and/or are susceptible to chemical cleavage by acids and enzymes in the gastrointestinal tract. Such antigens include those associated with or responsible for the induction of auto-immune diseases, clinical (allergic) hypersensitivities, and allograft rejection, and subunits or extracts therefrom; or recombinantly generated whole proteins, subunits or fragments thereof; or any combination thereof.

BRIEF DESCRIPTION OF THE DRAWINGS

The details of the present invention will be more fully described in connection with the accompanying drawings, in which.

DETAILED DESCRIPTION OF THE INVENTION

Figure 1:
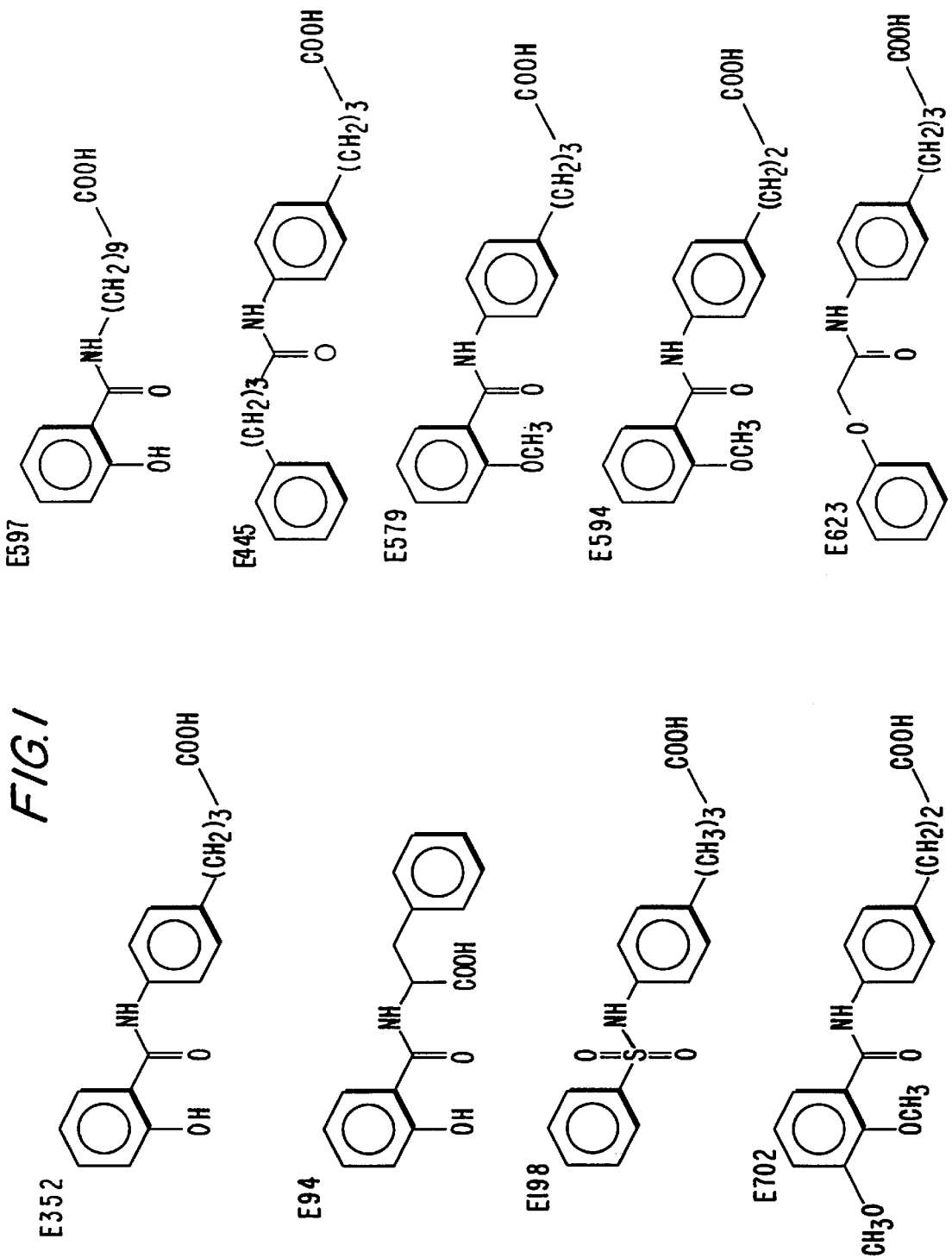
FIG. 1 provides formulas of preferred derivatized amino acids useful in the invention.

The present invention uses readily available and inexpensive delivery agents to provide mammals with oral tolerance to antigens. Oral tolerance is characterized as a state of antigen-specific systemic immunological hyporesponsiveness induced by the feeding of an antigen. Oral tolerance generally results from large or chronic doses of antigens. As pointed out hereinabove, the present invention is directed to methods and pharmaceutical formulations comprising an antigen and an derivatized amino acid or salt delivery agent useful to induce oral tolerance to the antigen when the antigen and delivery agent are fed simultaneously. The delivery agents allow the administration of lower or fewer doses of antigen than are required to induce the same degree of systemic immune suppression with the antigen alone. The immune responses involved include, but are not limited to, systemic antibody production and delayed-type hypersensitivity reactions.

The induction of oral tolerance may be applied clinically for the prevention or treatment of auto-immunie diseases and clinical (allergic) hypersensitivities, and for the prevention of allograft rejection.

Antigens

Antigens suitable for use in the present invention include, but are not limited to, synthetic or naturally derived proteins and peptides, and particularly those which by themselves require high doses to induce oral tolerance; carbohydrates including, but not limited to, polysaccharides; lipopolysaccharides; and antigens isolated from biological sources such as, for example, those associated with or responsible for the induction of auto-immune diseases, clinical (allergic) hypersensitivities, and allograft rejection and subunits or extracts therefrom; or any combination thereof.

Special mention is made of antigens associated with the autoimmune diseases of multiple sclerosis, lupus erthymetosis, scleroderma, uveitis, insulin-dependent diabetes mellitus or arthritis. In addition, self-antigens include: nucleic acid; oligodeoxynucleotide; thyroglobulin; thyroid cell surface or cytoplasm; parietal cell; adrenal cell; epidermal cell; uvea cell; basement membrane cell; red cell surface; platelet cell surface; muscle cell; thymus myeloid cell; mitochondria; secretory duct cell; deoxyribonucleic acid-protein; acetylcholine receptor substance; insulin; central nervous system antigens such as, myelin basic protein, proteolypid protein, and myelin oligodendrocyte glycoprotein; and other normal hormone and tissue factors.

Allergens include: benzylpenicilloyl, insulin, ovalbumin, lactalbumin, bermuda grass pollen, timothy grass pollen, orchard grass pollen, and combinations of grass pollen, ragweed pollen, ragweed antigen E, birch tree pollen, bee venom, snake venom, horse dander, cat epithelial, haddock, house dust mite, *Chrysanthemum leucanthemum, Alternari tenuis,* trypsin, chymotrypsin, dry rot, baker's yeast, tetanus toxoid, diphtheria toxin, ficin and derivatives thereof.

DELIVERY AGENTS

The delivery agents employed in the practice of the present invention are derivatized amino acids or salts thereof. The derivatized amino acids include amino acid amides.

Amino acids which may be used to prepare the delivery agents employed in the methods and compositions of the invention include any carboxylic acid having at least one free amino group, including both naturally occurring and synthetic amino acids. Many amino acids and amino acid esters are readily available from a number of commercial sources such as Aldrich Chemical Co. (Milwalkee, Wis., USA); Sigma Chemical Co. (St Louis; Mo., USA); and Fluka Chemical Corp. (Ronkonkoma, N.Y., USA). Methods useful for derivatization of the amino acids identified herein are disclosed in U.S. Pat. No. 5,958,457, filed May 10, 1995; U.S. Pat. No. 5,709,861, filed Jan. 13, 1995; and PCT/US96/00871, filed Jan. 16, 1996, published Jul. 18, 1996 under International Publication Number WO96/21464.

The preferred naturally occurring amino acids used for derivatzation to produce the delivery agents used in the methods and compositions hereof in the present invention are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, hydroxyproline, γ-carboxyglutamate, phenylglycine, or o-phosphoserine. It is particularly desirable to utilize arginine, leucine, lysine, phenylalanine, tyrosine, tryptophan, valine, or phenylglycine as substrates.

The preferred non-naturally occurring amino acids which may be derivatized for use as delivery agents in the present invention are β-alanine, α-amino butyric acid, γ-amino butyric acid, γ-(aminophenyl)butyric acid, α-amino isobutyric acid, 6-aminocaproic acid, 7-amino heptanoic acid, β-aspartic acid, aminobenzoic acid, aminophenyl acetic acid, aminophenyl butyric acid, γ-glutamic acid, cysteine (ACM), ε-lysine, ε-lysine, methionine sulfone, norleucine, norvaline, ornithine, d-ornithine, p-nitro-phenylalanine, hydroxy proline, 1,2,3,4,-tetrahydroisoquinoline-3-carboxylic acid and thioproline.

Although the present invention encompasses the use of delivery agents prepared by derivatization of any of the amino acids discussed above, preferred derivatized amino acids to employ in the methods and formulations of the present invention are those of Formulas I and II above. Particularly preferred derivatized amino acids useful as delivery agents are those referred to above and in FIG. 1 as E352; E94; E198; E702; E597; E445; E579; E594; and E623.

ADJUVANTS

Adjuvants which assist in inducing tolerance include lipopolysaccharides (LPS) and cholera toxin β-subunit.

Pharmaceutical Formulations

Delivery of pharmaceutical formulations comprised of an antigen and a delivery agent (with or without an adjuvant), with the delivery agent or agents described herein are, preferably a derivatized amino acid of Formulas I and II administered in a dose of about 100–1,000 mg/kg of body weight, results in the induction of oral tolerance.

In one embodiment of the present invention, the derivatized amino acids or salts thereof may be used as delivery agents by simply mixing one or more derivatized amino acids or salts thereof with the antigen (with or without adjuvant) prior to oral administration. In another embodiment, the derivatized amino acids or salts thereof may be used to form microspheres or microcapsules containing the antigen (with or without adjuvant).

Microspheres containing antigen with or without adjuvant can generally be of the matrix form or the microcapsule form. The matrix form includes both a hollow matrix sphere in which the delivery agent forms a matrix shell around a hollow center with the antigen (with or without adjuvant) distributed throughout the matrix and a solid matrix sphere in which the delivery agent forms a spherical matrix continuum in which the antigen (without or without adjuvant) is distributed. The microcapsule form, on the other hand, is one in which the encapsulated antigen (either with or without adjuvant) is either in solution or in solid form, with the delivery agent forming a shell around the encapsulated material.

The formulations of the present invention may also include one or more enzyme inhibitors. Such enzyme inhibitors include, but are not limited to, compounds such as actinonin, aprotinin or epiactinonin and derivatives thereof. Derivatives of these compounds are disclosed in U.S. Pat. Nos. 5,958,457 and 5,709,861; and in PCT/US96/00871, International Publication Number WO96/21464.

The formulations of the present invention may be formulated into oral dosage units by the addition of one or more excipients, diluents, disintegrants, lubricants, plasticizers, colorants, or dosing vehicles. Preferred oral unit dosage forms include, but are not limited to, tablets, capsules, or liquids. The oral unit dosage forms can include biologically effective amounts of the antigen (with or without a biologically effective amount of an adjuvant) but can include less than such amounts if multiple unit dosage forms are to be used to administer a total dosage of the antigen with or without adjuvant. Oral unit dosage forms are prepared by methods conventional in the art.

The delivery agents of the present invention do not alter the physiological and biological properties of the antigen or the adjuvant. Furthermore encapsulation, if used, need not alter the structure of the antigen.

Inducing Oral Tolerance to Autoimmune Antigens

Also provided herein is a demonstration that the delivery agents of the invention are capable of promoting suppression of EAE through oral tolerance. EAE is widely used as a model for human autoimmune inflammatory demyelinating diseases. (See BACKGROUND above.) It is proposed that the derivatized amino acid delivery agents of the invention act by increasing the fraction of an administered dose of MBP that is absorbed across the GI epithelia. This is very significant, since tolerance is known to be a highly dose-dependent phenomenon. The presence of delivery agents may also lead to a decrease in the variability in responses that accompanies normal GI absorption. The invention thus provides for modulation of immunogenic response, and thus clinical disease, by oral administration of autoantigens accomplished in the presence of delivery agents using smaller or fewer administered doses than are required with the antigen alone. It will be understood that the methods and compositions of the invention are not limited by the foregoing possible mode of action.

EXAMPLES

The following examples are intended to illustrate the invention, without limiting its scope.

Example 1

Single Dose Oral Administration of Sheep Red Blood Cells with Delivery Agent

Five female BALB/c mice were fed a single dose suspension of $2.5 \times 10^9$ sheep red blood cells (SRBC)+E94 (600 mg/Kg) in Phosphate Buffered Saline (PBS), 0.1 M phosphate and 0.15 M sodium chloride, pH 7.2. Seven days after completion of oral dosing, mice were primed by footpad injection of $1 \times 10^7$ SRBC. They were bled on day 14. On day 21 the mice were tested in a Delayed Type Hypersensitivity (DTH) test through challenge by injection in the footpad not previously used in priming with $1 \times 10^8$ SRBC. Footpad thickness was measured before and 24 hours after challenge using a Vernier caliper. On day 28 they were bled again. Sera were placed into Eppendorf tubes and assayed for anti-SRBC IgM (days 14 and 28) and anti-SRBC IgG (day 28) by the direct and indirect hemagglutination assays, respectively. (See assay description below.) Prior to assaying, the samples were heat inactivated at 56/C. for 60 minutes. Assay data for Example 1 are found in FIG. 2.

Direct Hemagglutination Assay for Anti-SRBC Serum IgM Antibodies a) Dilute $10\mu$ of sera with $190\mu$ of PBS, pH 7.2 (1/20)
b) On a rigid, U-bottom microtiter plate, mark wells across the rows for dilutions of samples 40; 80; 160; . . . 81,920
c) Place $50\mu$ of PBS in each well
d) In the first well of duplicate rows, add $50\mu$ of heat-inactivated, I/20 diluted sera (first well=1/40) Leave two rows for controls: Mixture of IgM+IgG positive controls (Rabbit anti-SRBC IgM and Rabbit anti-SRBC IgG), $25\mu$ each diluted I/20 in PBS
e) Serially 2× dilute the sera or controls ($50\mu$) across each row
f) Add $50\mu$ of 0.5% SRBC to each well
g) Cover with pressure-sensitive adhesive plate sealer (COSTAR™)Shake briefly at low speed to mix
h) Incubate overnight at room temperature, taking care not to disturb the plate at all
i) Carefully examine for IgM hemagglutination patterns. A positive response appears as a uniform coating of cells adhering to the bottom of wells. A negative response appears as a tight button of settled cells that will stream down if the plate is tilted.
j) Record average of duplicates.
k) To assay for anti-SRBC IgG antibodies DO NOT empty wells. Go on to perform indirect HA assay on the same plate.

Indirect Hemagglutination Assay for Non-agglutinating Anti-SRBC Serum IgG Antibodies a) In a 15 ml tube, add 11µ of goat anti-mouse IgG (Fc$_y$ specific) (2.3 mg/ml) to 5.05 ml PBS (1/460 dilution; approximate amount needed per plate) In a second tube, add 4µ of goat anti-rabbit IgG (F$_c$ specific) to 1.8 ml of PBS approximate amount needed (per plate)
b) Add 50µ of diluted goat anti-mouse IgG (FC$_y$ specific) to the sample wells (0.25 µg per well) Add 0.25 mg of goat anti-rabbit IgG (F$_c$ specific) to each control well
c) Cover with pressure-sensitive adhesive plate sealer (COSTAR™)
d) Shake slowly and briefly to mix
e) Incubate 2 hours at room temp. followed by overnight at 4/C.
f) Carefully examine for IgG hemagglutination titers
g) Record average of duplicates.

Comparative Example A

Single Dose Oral Administration of SRBC Alone

Five female BALB/c mice were fed a single dose suspension of SRBC alone with no delivery agent precisely as described in Example 1. The mice were bled and assayed as described in Example 1. Assay data for Comparative Example A are found in FIG. 2.

Example 2

Oral Administration of Sheep Red Blood Cells for Five Consecutive Days with Delivery Agent Five female BALB/c mice were fed a suspension of $2.5 \times 10^9$ sheep red blood cells (SRBC)+E94 (600 mg/Kg) in Phosphate Buffered Saline (PBS) for five consecutive days. The mice were bled and assayed as described in Example 1. Assay data for Comparative Example B are found in FIG. 2.

Comparative Example B

Administration of SRBC Alone for Five Consecutive Days

Five female BALB/c mice were fed a suspension of SRBC alone with no delivery agent for five consecutive days as described in Example 2. The mice were bled and assayed as described in Example 1. Assay data for Comparative Example B are found in FIG. 2.

Comparative Example C

Administration of SRBC Alone for Fifteen Consecutive Days

Five female BALB/c mice were fed a suspension of SRBC alone with no delivery agent for fifteen consecutive days as described in Comparative Example B. The mice were bled and assayed as described in Example 1. Assay data for Comparative Example B are found in FIG. 2.

Comparative Example D

Single Dose Oral Administration of Saline Alone (No SRBC)

Five female BALB/c mice were fed a single oral dose of saline solution with no delivery agent as an unfed control. The mice were bled and assayed as described in Example 1. Assay data for Comparative Example D are found in FIG. 2.

Figure 2:
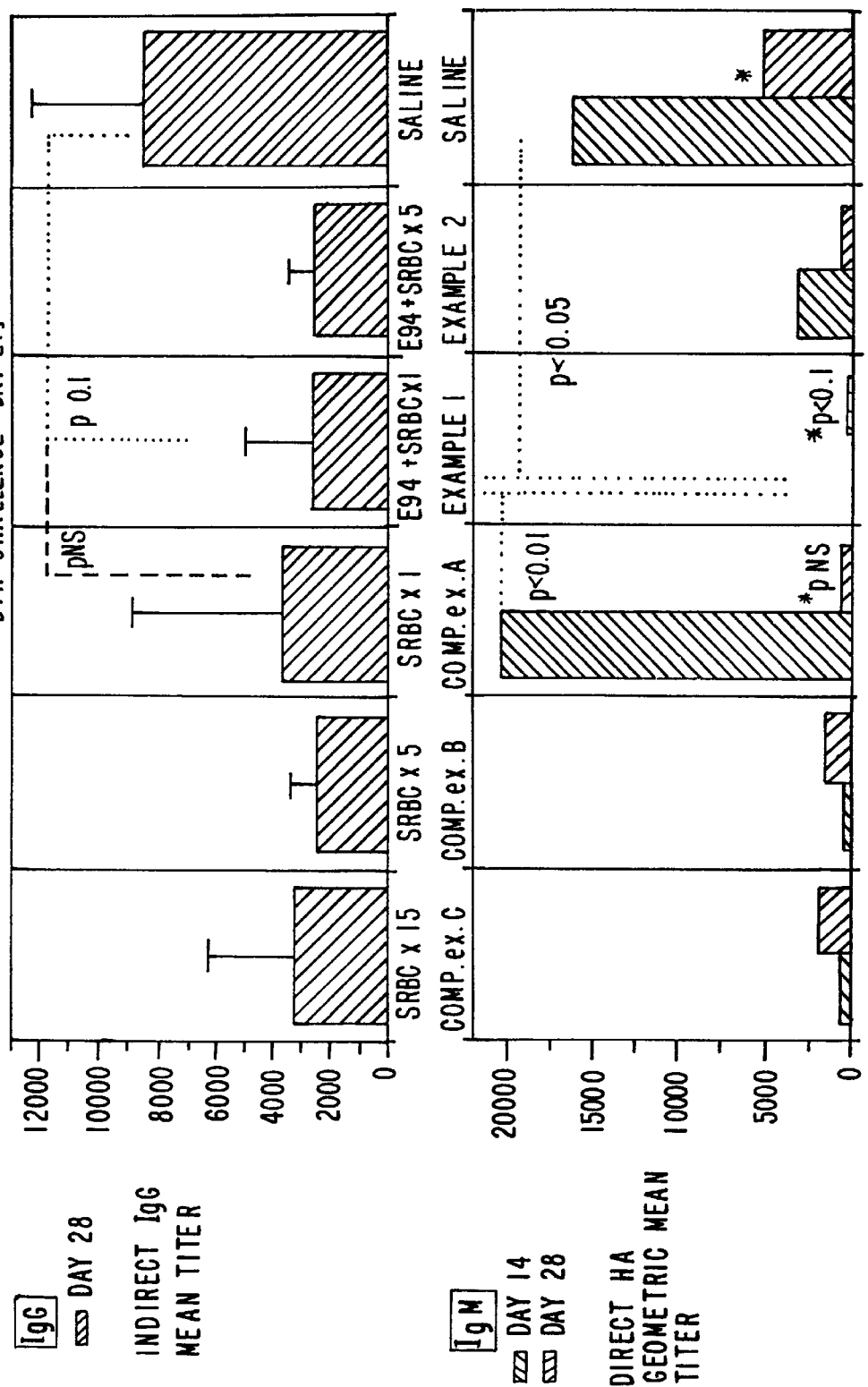
FIG. 2 is a graphic representation of the titer of serum anti-sheep red blood cell (anti-SRBC) IgG antibodies (determined through the indirect IgG assay) and IgM antibodies (determined through the direct IgM assay) in mice fed SRBC with or without salicyloyl-phenylalanine (E94) derivatized amino acid delivery agent in accordance with Examples 1 and 2 and Comparative Examples A, B, C, and D.

As can be seen in FIG. 2 (Examples 1 and 2; and Comparative Examples A, B, C and D) a single dose of SRBC in the presence of E94 delivery agent (Example 1) suppressed IgM on Day 14 relative to unfed control (Comparative Example D) significantly more than without delivery agent (Comparative Example A), and even lower than 15 doses of SRBC alone (Comparative Example C). On Day 28, IgM for Example 1 (E94+SRBC×1) was still lower than that for the Comparative Example D control (90% significance) while no other group was significantly different from the Comparative Example D control.

FIG. 2 also shows that for IgG, on Day 28, the Example 1 (E94+SRBC×1) group was lower than the Comparative Example D control (90% significance) while no other groups were significantly different from the Comparative Example D control.

Example 3

Oral Administration of Influenza Antigen with Delivery Agents After Priming

Eight OF-1 female mice were primed subcutaneously with a low dose (5 µg per mouse) of vaccine alone (to mimic a non-naive population) on day 0, followed by oral dosing on day 21 with 60 µg of Influenza antigen per mouse in solution with 750 mg/kg of E94. Sera were collected every two weeks, pooled, and assayed for hemagglutination inhibition. (See assay description below.) Assay data for Example 3 are found in FIG. 3.

Hemagglutination Inhibition Assay for Anti-HA Antibodies:

A. Hemagglutination Assay to Determine Virus HA Titer
  1) Use hard plastic-U-bottom plates.
  2) Mark wells 1–10 as 1/10, 1/20 . . . to 1/5120. Mark #12A and 12B as controls
  3) In a tube, dilute virus suspension 1/10 with PBS.
  4) Add 50 µl PBS to each well from #2 to #10 in duplicate rows.
  5) Add 100 µl of diluted virus suspension to well #1.
  6) Serially 2× dilute 50 µl of the virus across plate until well #10, mixing 7× per dilution.
  7) Add 50 µl of well-suspended 0.5% chicken (or sheep) [WHICH ONE?] red blood cells to each well (including control).
  8) Cover plate with sealer.
  9) Shake briefly on titer plate shaker.
  10) Incubate without shaking at room temperature for 30 minutes.
  11) Be sure that control wells show a negative pattern (compact settled drip). If not, wait until they do so.
  12) Immediately note the patterns in each well.
  13) Record the HA titer of the virus as the highest dilution which resulted in complete agglutination. If duplicates differ by one dilution, take the average. If they differ by more than one dilution, repeat the assay.
  14) This titer provides the dilution of virus suspension which contains one HA unit per 50 µl. Divide this titer by 8 to get the dilution which will contain 4 HA units per 0.025 µl for the actual Hemagglutination Inhibition (HI) assay.

On the day of the HI assay, prepare just enough diluted virus for back-titration. If the back-titration assay is satisfactory, dilute enough virus for the HI assay of the sera samples.

B. Hemagglutination Inhibition (HI) Assay of Sera

RDE* treat all test sera, reference sera and negative control sera on the day before the HI assay will be done.

1. RDE* Treatment of Sera to Remove Non-specific Inhibitors
   a) Reconstitute RDE (Accurate Chemical and Scientific Corp., Westbury, N.Y.) immediately before use.
   b) Add 100 µl serum and 300 µl RDE to 2 ml Eppendorf tube Vortex briefly
   c) Incubate at 37/C. overnight
   d) Prepare 2.5% sodium citrate solution: 2.5 g sodium citrate plus distilled water q.s. to 100 ml
   e) Add 300 µl sodium citrate solution to the sample tube
   f) Incubate at 56/C. for 30 minutes
   g) Add 300 µl of PBS. This will result in a 1/10 starting dilution of serum.

2. HI Assay
   A. Back-titration of virus.
      a) In a hard plastic plate, add 100 µl of PBS to duplicate wells 1–5 (rows A and B) and to two control wells
      b) Add 50 µl of the diluted virus suspension (part A #15 above) to well 1 of each row
      c) Serially 2× dilute across to wells A5 and B5
      d) Add 50 µl of 0.5% SRBC to all wells, including the control wells
      e) Cover, shake briefly, and incubate 30 minutes
      f) The first 3 wells should be completely agglutinated, 4 and 5 should be partially or not at all agglutinated. If this is not the case, the virus stock should be diluted appropriately to correct for this difference and re-assayed.
   B. HI assay:
      1. Use flexible plates. Mark columns for duplicate dilution series of each test and control serum sample (normal naive serum and positive reference anti-serum). The plate should have 11 columns per row for dilutions plus column 12 for RBC alone.
      2. To all wells, except column 1, add 25 µl of PBS.
      3. To column 1 wells, add 50 µl of the appropriate RDE-treatment serum (test, positive, or negative control) sample.
      4. Serially 2× dilute 25 µl of the sera across to column 11, mixing 7× per dilution.
      5. Add 25 µl of diluted virus (containing 4 HA units per 25 µl) to all serum dilution wells, columns 1–11. Add 25 µl of PBS to column 21.
      6. Cover plate, mix briefly on shaker, and incubate at r.t. for 30 minutes.7.
      7. Add 50 µl of well-suspended 0.5% red blood cells to all wells, including the RBC control wells (column 12). Cover and shake briefly.
      8. Incubate at room temperature for 30–45 minutes, until RBC controls show a compact, negative pattern.
      9. Read patterns immediately.
      10. Negative control (naive) serum: all wells should show complete agglutination (i.e. no inhibition since there is no anti-HA antibody).
      11. Positive control (reference) serum; should see uniform inhibition in the dilution series up to the theoretical titer of the reference serum.

Comparative Example

Single Dose Oral Administration of Influenza Antigen Alone

Eight OF-1 female mice were treated and fed a single dose preparation of influenza antigen alone with no delivery agent as described in Example 3. The mice were bled and assayed as described in Example 3. Assay data for Comparative Example E are found in FIG. 3.

Figure 3:
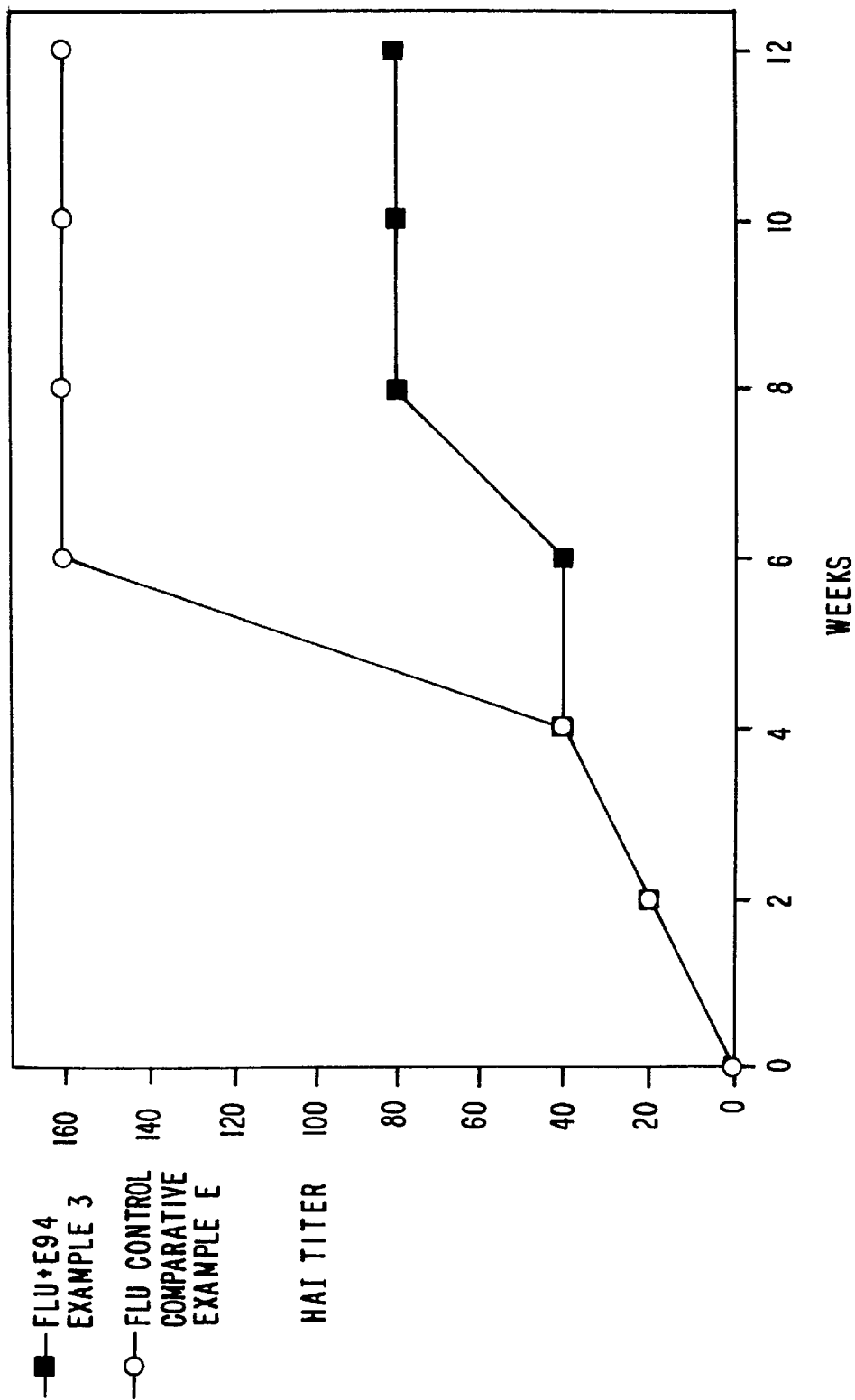
FIG. 3 is a graphic representation of the titer of anti-influenza antibodies (determined through the hemagglutination inhibition assay) present in pooled sera of mice pre-immunized with influenza antigen and fed influenza antigen with or without salicyloyl-phenylalanine (E94) derivatized amino acid delivery agent in accordance with Example 3 and Comparative Example E.

As can be seen in FIG. 3 (Example 3 and comparative Example E) a single dose of influenza antigen with E94 delivery agent (Example 3) suppressed the production of anti-influenza antibodies relative to control fed only influenza antigen (Comparative Example E) by more than 2 fold.

Virtually all adult humans have been exposed to Influenza at one or more times. Thus, most people have some levels of pre-existing immunity to Influenza. This preexisting condition will influence their susceptibility to infection to cross-reacting strains of the disease. To simulate the effects of immunization with oral vaccine in this non-naive population, the mice were pre-immunized with a lower dose of antigen than would be required to fully immunize them.

Example 4

Oral Administration of Influenza Antigen with Delivery Agents

Ten BALB/c mice were administered a single oral dose of 15 µg of influenza antigen [influenza vaccine A/Johannesburg/39/94 (H3N2)] per mouse with 500 mg/kg of E352. Sera were collected every two weeks, pooled, and assayed for anti-hemagglutinin (HA) IgG. (See assay description below.) Assay data for Example 4 are found in FIG. 4.

ELISA For Determining Anti-HA IgG Isotype Antibodies in Serum

1. Coat plates with HA antigen, 10 µg/mL in carbonate buffer.
2. Wash×4.
3. Block with Superblock™ or 1/10 diluted Bovine Serum Albumin (BSA).
4. Add 100 µL per well of diluent (Superblock™ or 1/15 diluted BSA) to all except the top row.
5. In the first row, add 150 µL per well of 1/100 diluted test serum in duplicate and serially dilute 3× down the plate. Leave 2 empty wells as background.
6. Incubate 2 hours at room temperature.
7. Wash×8.
8. To each well, add 100 µl of IgG isotype-specific anti-mouse alkaline-phosphatase conjugated antibody (diluted with 4% PEG 6000).20. Incubate overnight at 4/C.
9. Wash×8.
10. Add 100 µL per well of p-nitrophenyl phosphate (pNPP) substrate solution and incubate in the dark with shaking for 30 minutes.
11. Read and record $OD_{405}$ after subtracting the background absorbance.

Comparative Example F

Oral Administration of Influenza Antigen Alone

Ten BALB/c mice were fed a single dose preparation of influenza antigen [influenza vaccine A/Johannesburg/39/94 (H3N2)] alone with no delivery agent as described in Example 4. The mice were bled and assayed as described in Example 4. Assay data for Comparative Example F are found in FIG. 4.

Figure 4:
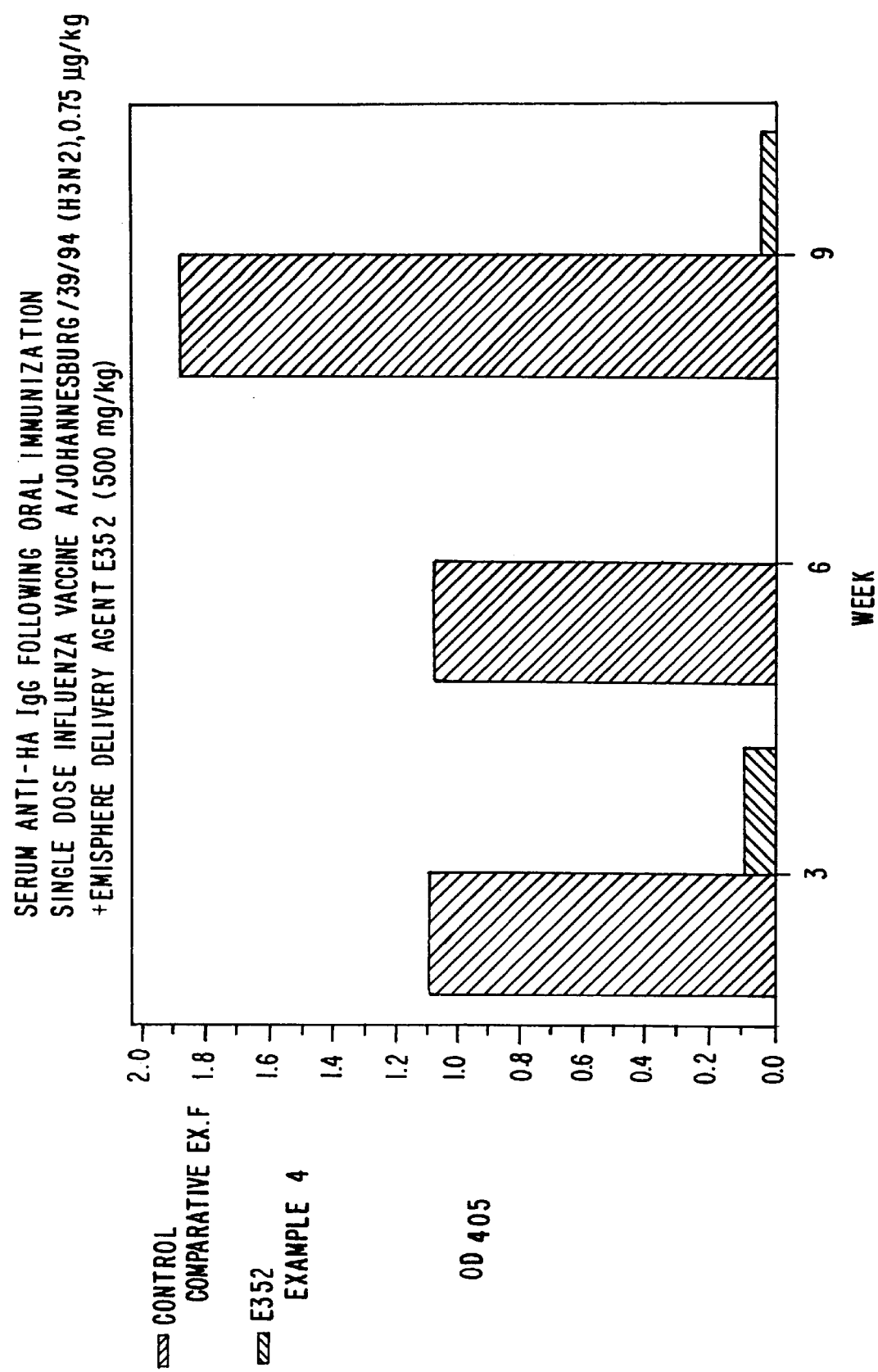
FIG. 4 is a graphic representation of the titer of serum anti-HA (influenza) IgG antibodies following single-dose feeding of influenza vaccine A/Johannesburg/39/94 (H3N2) with or without N-salicyloyl-4-amino-phenyl butyric acid (E352) derivatized amino acid delivery agent in accordance with Example 4 and Comparative Example F.

As can be seen in FIG. 4 (Example 4 and Comparative Example F) a single does of influenza antigen with E352 delivery agent (Example 4) significantly suppressed the production of anti-influenza antibodies relative to control fed only influenza antigen.

Example 5

Two Dose Oral Administration of Ovalbumin with Delivery Agent

A stock solution was prepared by dissolving Ovalbumin, 10 mg/ml, in 10 mM phosphate buffer (pH 7.4). This solution was diluted with buffer to provide 1.0 mg in a volume of 0.2 ml. Ten BALB/c female mice were administered two oral doses of 1 mg ovalbumin per mouse with 600 mg/kg of E94 delivery agent at weeks 0 and 4.

Systemic challenge was achieved by intramuscular (IM) injection of 2 mg/ml ovalbumin with 50% Complete Freund's Adjuvant (CFA) at week 9. Serum samples were collected at week 12 and assayed for anti-ovalbumin total IgG isotypes as described in Example 4 utilizing ovalbumin antigen instead of HA antigen. Assay data for Example 5 are found in FIG. 5.

Comparative Example G

Two Dose Oral Administration of Ovalbumin Alone

Ten BALB/c female mice were fed two oral doses of 1 mg ovalbumin per mouse alone with no delivery agent at weeks 0 and 4 as described in Example 5. The mice were challenged, bled and assayed as described in Example 5. Assay data for Comparative Example G are found in FIG. 5.

Figure 5:
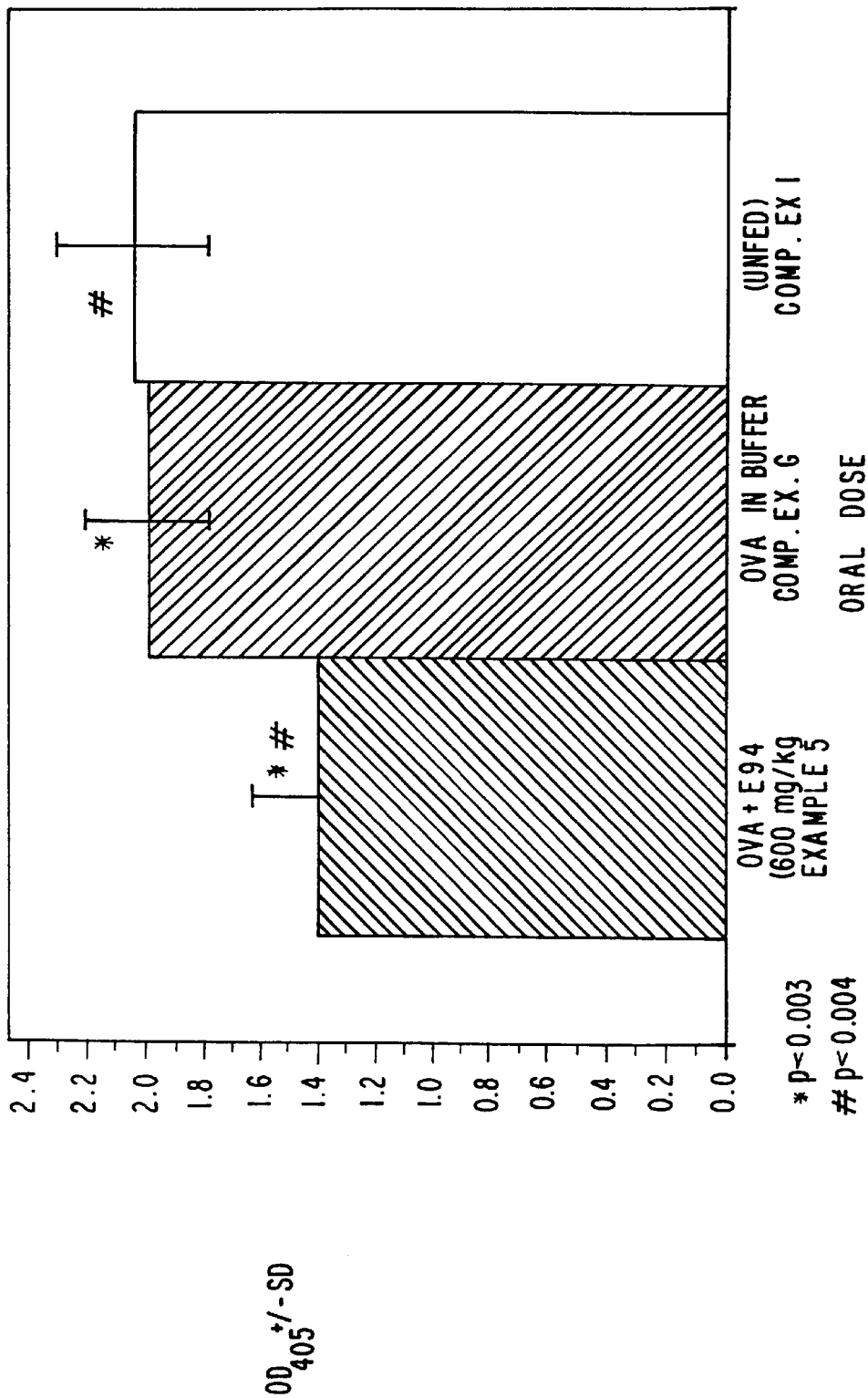
FIG. 5 is a graphic representation of the titer of serum anti-ovalbumin IgG antibodies at week 12 in mice fed two doses of ovalbumin at weeks 0 and 4 with or without salicyloyl-phenylalanine (E94) derivatized amino acid delivery agent and challenged intramuscularly at week 9 with ovalbumin and Complete Freund's Adjuvant (CFA) in accordance with Example 5 and Comparative Examples G and I.

FIG. 5 illustrates the anti-Ova IgG response in mice immunized orally with two doses of 1 mg Ovalbumin each with or without delivery agent E94, four weeks apart. They were then challenged intramuscularly with Ovalbumin in complete Freund's adjuvant. The response to the challenge with antigen alone (Comp. Ex. G) was the same as in mice given the intramuscular dose alone. However, following feeding in the presence of delivery agent (Ex. 5), the response was significantly suppressed compared to both unfed and antigen-alone fed (Comp. Ex. G) animals. This indicates induction of tolerance in the presence of delivery agent following feeding of a dose which is non-tolerizing in the absence of the delivery agent.

Example 6

Single Dose Oral Administration of Ovalbumin with Delivery Agent

A stock solution of ovalbumin was prepared by dissolving Ovalbumin, 125 mg/ml, in 10 mM phosphate buffer (pH 7.4). This solution was used to provide 25 mg in a volume of 0.2 ml. Five BALB/c mice were administered a single oral dose of 25 mg ovalbumin per mouse with 600 mg/kg of E94 delivery agent.

Challenge was achieved by subcutaneous (SC) injection of 0.1 mg ovalbumin with 50% Complete Freund's Adjuvant (CFA) at week 1. Serum samples were collected at week 4 and assayed for anti-ovalbumin total IgG isotypes as described in Example 5. Assay data for Example 6 are found in FIG. 6.

Comparative Example H

Oral Dose Administration of Ovalbumin Alone

Five BALB/c female mice were fed a single oral dose of 25 mg ovalbumin per mouse alone with no delivery agent as described in Example 6. The mice were challenged, bled and assayed as described in Example 6. Assay data for Comparative Example E are found in FIG. 6.

Comparative Example I

Unfed Mice for Control

Five BALB/c female mice were fed nothing for use as a control. The mice were challenged, bled and assayed as described in Example 5 for data described in FIG. 5. The mice were challenged, bled and assayed as described in Example 6 for data described in FIG. 6.

Figure 6:
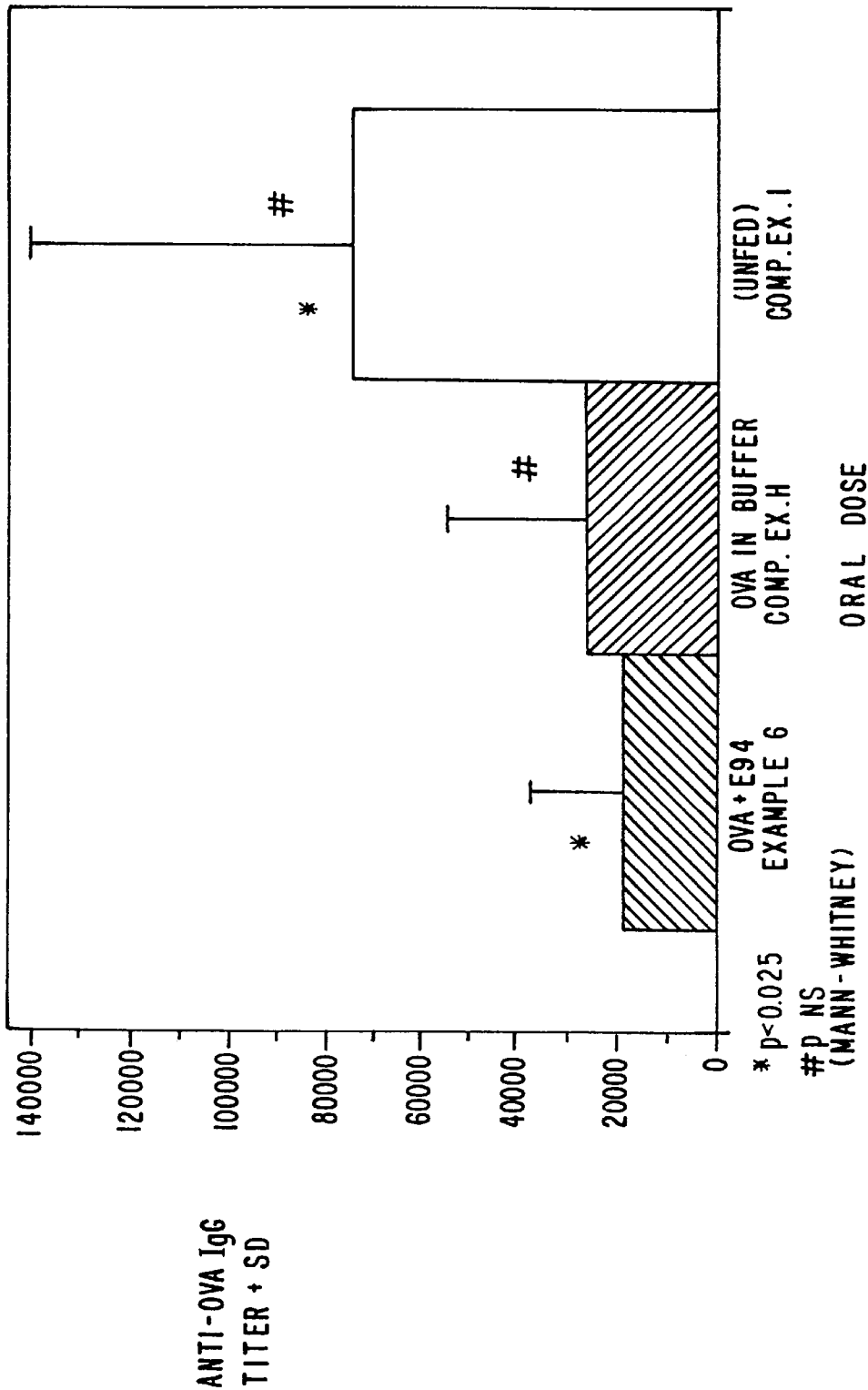
FIG. 6 is a graphic representation of the titer of serum anti-ovalbumin IgG antibodies at week 4 in mice fed a single dose of ovalbumin with or without salicyloyl-phenylalanine (E94) derivatized amino acid delivery agent and challenged subcutaneously at week 1 with ovalbumin in CFA in accordance with Example 6 and Comparative Examples H and I.

FIG. 6 illustrates that animals fed 25 mg Ovalbumun with delivery agent E94 and then challenged subcutaneously one week later with Ovalbumin in complete Freund's adjuvant show significantly suppressed serum anti-Ova IgG titers than those which were not pre-fed. While mice fed antigen alone were also suppressed (Comp. Ex. H), this suppression was not statistically significant, while that induced in the presence of E94 (Ex. 6) was significant. Thus, E94 allowed a more consistent suppression of antibody induction than the antigen alone.

Example 7

Single Dose Oral Administration of Sheep Red Blood Cells with Delivery Agent Five female BALB/c mice were fed a single dose suspension of $2.5 \times 10^9$ sheep red blood cells (SRBC)+E594 (600 mg/Kg) in Phosphate Buffered Saline (PBS), 0.1 M phosphate and 0.15 M sodium chloride, pH 7.2. Seven days after completion of oral dosing, mice were primed by footpad injection of $1 \times 10^7$ SRBC. They were bled on day 14. Sera were placed into Eppendorf tubes and assayed for anti-SRBC IgG (day 14) by the indirect hemagglutination assays. (See assay description in Example 1 above.) Prior to assaying, the samples were heat inactivated at 56° C. for 60 minutes. Assay data for Example 7 are found in FIG. 7.

Comparative Example J

Single Dose Oral Administration of SRBC Alone

Five female BALB/c mice were fed a single dose suspension of SRBC alone with no delivery agent as described in Example 7. The mice were bled and assayed as described in Example 7. Assay data for Comparative Example J are found in FIG. 7.

Comparative Example K

Single Dose Oral Administration of Saline Alone (No SRBC)

Five female BALB/c mice were fed a single oral dose of saline solution with no delivery agent as an unfed control. The mice were bled and assayed as described in Example 7. Assay data for Comparative Example K are found in FIG. 7.

Figure 7:
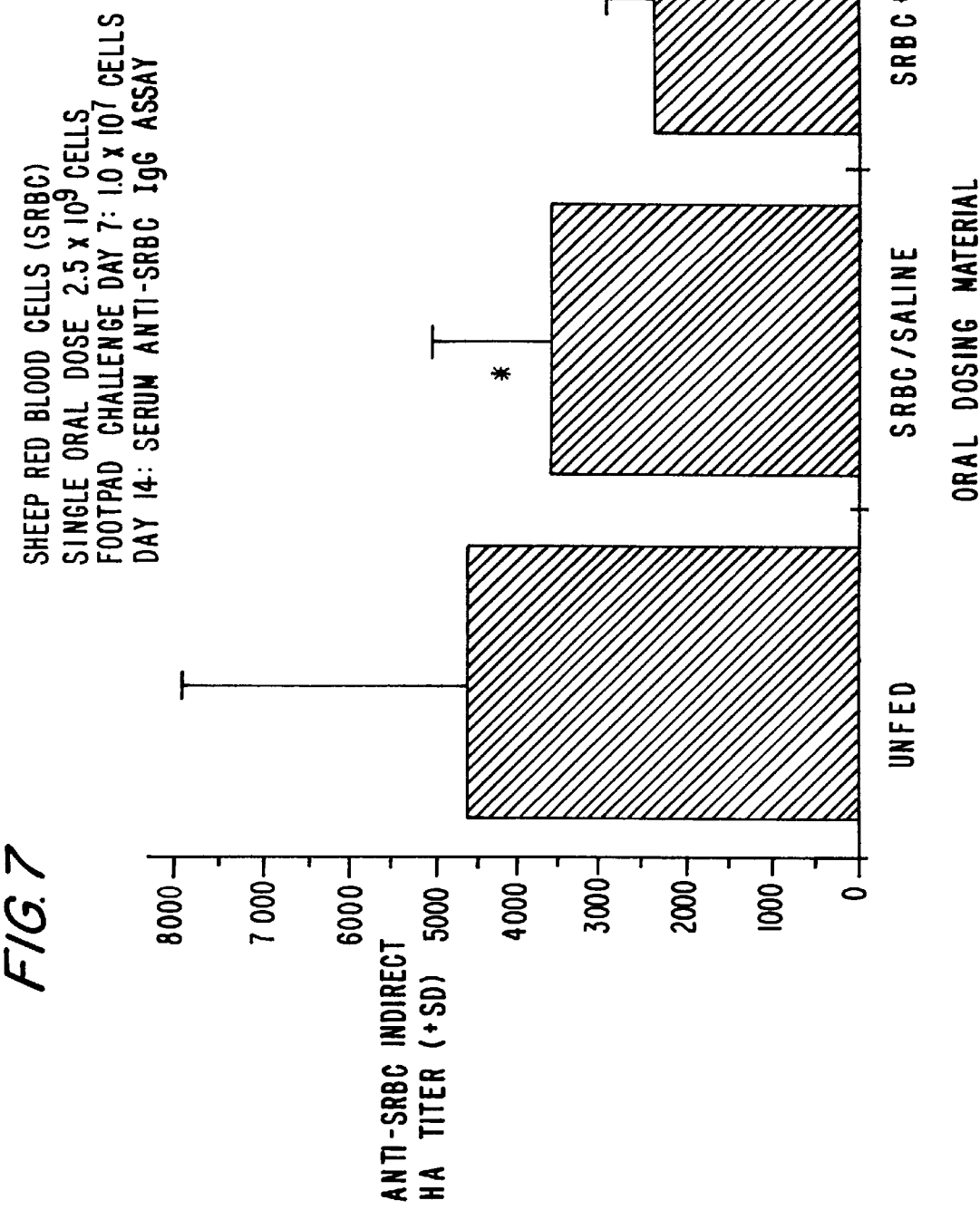
FIG. 7 is a graphic representation of of the titer of serum anti-sheep red blood cell (anti-SRBC) IgG antibodies (determined through the indirect IgG assay) on day 14 in mice fed SRBC with or without 3-[4-(N-2 methoxybenzoyl)]aminophenyl propionic acid (E594) derivatized amino acid delivery agent in accordance with Example 7 and Comparative Examples J and K.

As can be seen in FIG. 7 (Example 7 and Comparative Examples J and K) a single dose of SRBC in the presence of E594 delivery agent (Example 7) suppressed IgG on Day 14 relative to unfed control (Comparative Example K) significantly more than without delivery agent (Comparative Example J.

Example 8

Single Dose Oral Administration of Sheep Red Blood Cells with Delivery Agent Five female BALB/c mice were fed a single dose suspension of $2.5 \times 10^9$ sheep red blood cells (SRBC)+E594

(600 mg/Kg) as described in Example 7. Seven days after completion of oral dosing, mice were primed by footpad injection of 1×10⁷ SRBC. On day 14. footpad thickness was measured according to the Delayed Type Hypersensitivity (DTH) method outlined in Example 1. The DTH data for Example 8 are found in FIG. 8.

Example 9

Single Dose Oral Administration of Sheep Red Blood Cells with Delivery Agent

Five female BALB/c mice were fed a single dose Suspension of $2.5 \times 10^9$ sheep red blood cells (SRBC)+E198 (600 mg/Kg) and tested for footpad thickness (DTH) as described in Example 8. The DTH data for Example 9 are found in FIG. 8.

Comparative Example L

Single Dose Oral Administration of Saline Alone (No SRBC)

Five female BALB/c mice were fed a single oral dose of saline solution with no delivery agent as an unfed control and tested for footpad thickness (DTH) as described in Example 8. The DTH data for Comparative Example L are found in FIG. 8.

Comparative Example M

Single Dose Oral Administration of SRBC Alone

Five female BALB/c mice were fed a single dose suspension of SRBC alone with no delivery agent and tested for footpad thickness (DTH) as described in Example 8. The DTH data for Comparative Example M are found in FIG. 8.

Figure 8:
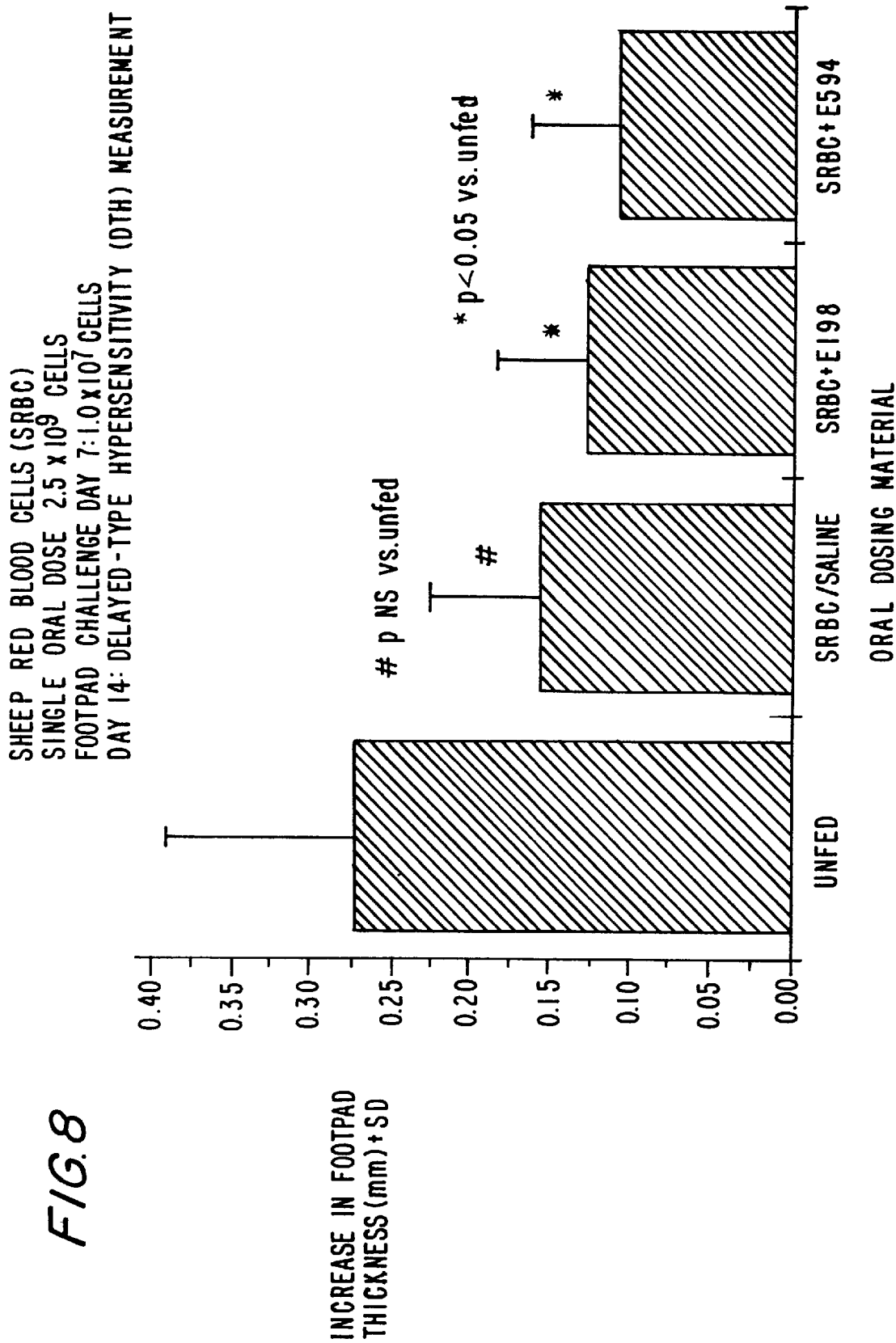
FIG. 8 is a graphic representation of footpad thickness in a DTH assay at day 14 in mice fed a single dose of SRBC with or without 4-[4-(N-benzenesulfonyl)]aminophenyl butyric acid (E198) and challenged in the footpad at day 7 in accordance with Examples 8 and 9 and Comparative Examples L and M.

As can be seen in FIG. 8 (Examples 8 and 9 and Comparative Examples L and M) a single dose of SRBC in the presence of E594 delivery agent (Example 8) or E198 delivery agent (Example 9) suppressed the DTH response on Day 14 relative to unfed control (Comparative Example L) significantly more than without delivery agent (Comparative Example M).

Example 10

Single Dose Oral Administration of Ovalbumin with Delivery Agent

A stock solution of ovalbumin was prepared by dissolving Ovalbumin, 10 mg/ml in 10 mM phosphate buffer (pH 7.4). This solution was diluted 2-fold and used to provide 1.0 mg in a volume of 0.2 ml. Five BALB/c mice were administered a single oral dose of 1.0 mg ovalbumin per mouse with 600 mg/kg of E702 delivery agent.

Challenge was achieved by subcutaneous (SC) injection of 0.1 mg ovalbumin with 50% Complete Freund's Adjuvant (CFA) at week 3. DTH assay was performed as described in Examples 1 and 8. Assay data for Example 10 are found in FIG. 9.

Comparative Example N

Single Oral Administration of Ovalbumin Alone

Five BALB/c female mice were fed a single oral dose of 1.0 mg ovalbulmin per mouse alone with no delivery agent as described in Example 10. The mice were challenged and assayed for DTH as described in Example 10. Assay data for Comparative Example N are found in FIG. 9.

Comparative Example O

Unfed Control

Five BALB/c female mice were fed a single oral dose of saline with no delivery agent as an unfed control. The mice were challenged and assayed for DTH as described in Example 10. Assay data for Comparative Example O are found in FIG. 9.

Figure 9:
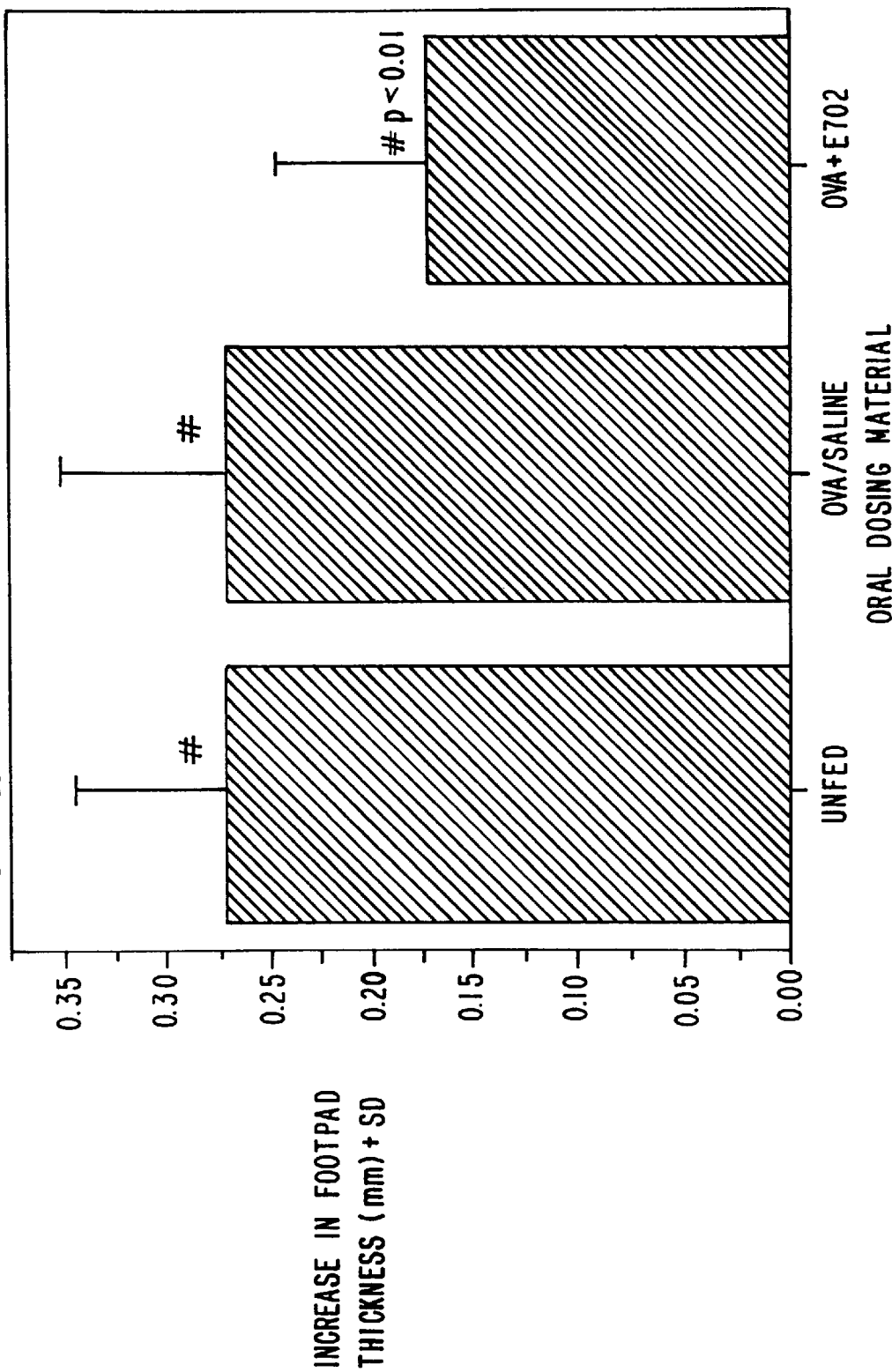
FIG. 9 is a graphic representation of footpad thickness in a DTH assay at week 5 in mice fed a single dose of ovalbulmin with or without 3-[4-(N-2,3-dimethoxybenzoyl)]aminophenyl propionic acid (E702) derivatized amino acid delivery agent and challenged subcutaneously at week 3 with ovalbumin in CFA in accordance with Example 10 and Comparative Examples N and O.

FIG. 9 illustrates that animals fed 1.0 mg Ovalbumun with delivery agent E702 and then challenged subcutaneously 3 weeks later with Ovalbumin in complete Freund's adjuvant show significantly suppressed response in the DTH than those which were not pre-fed. Mice fed antigen alone at this dosage were not suppressed (Comparative Example N).

Example 11

Use of Delivery Agents in the MBP/EAE Model for Oral Tolerance Induction

Groups of five female Lewis rats were given one or five oral doses of Myelin Basic Protein (MBP, 1.0 mg per dose every 2–3 days) or a single oral dose of 1.0 mg of MBP together with delivery agents E94, E352 or E702. Two days after the (last) oral dose, all groups were challenged in the footpad with 0.05 mg of MBP emulsified with Complete Freund's Adjuvant containing Mycobacterium tuberculosis H37Ra, 4 mg/ml. Clinical signs of disease were observed starting on Day 11 after the challenge and rated on a scale of 0 (no disease) to 5 (death). Data for Example 11 are provided in FIGS. 10, 11 and 12.

Figure 10:
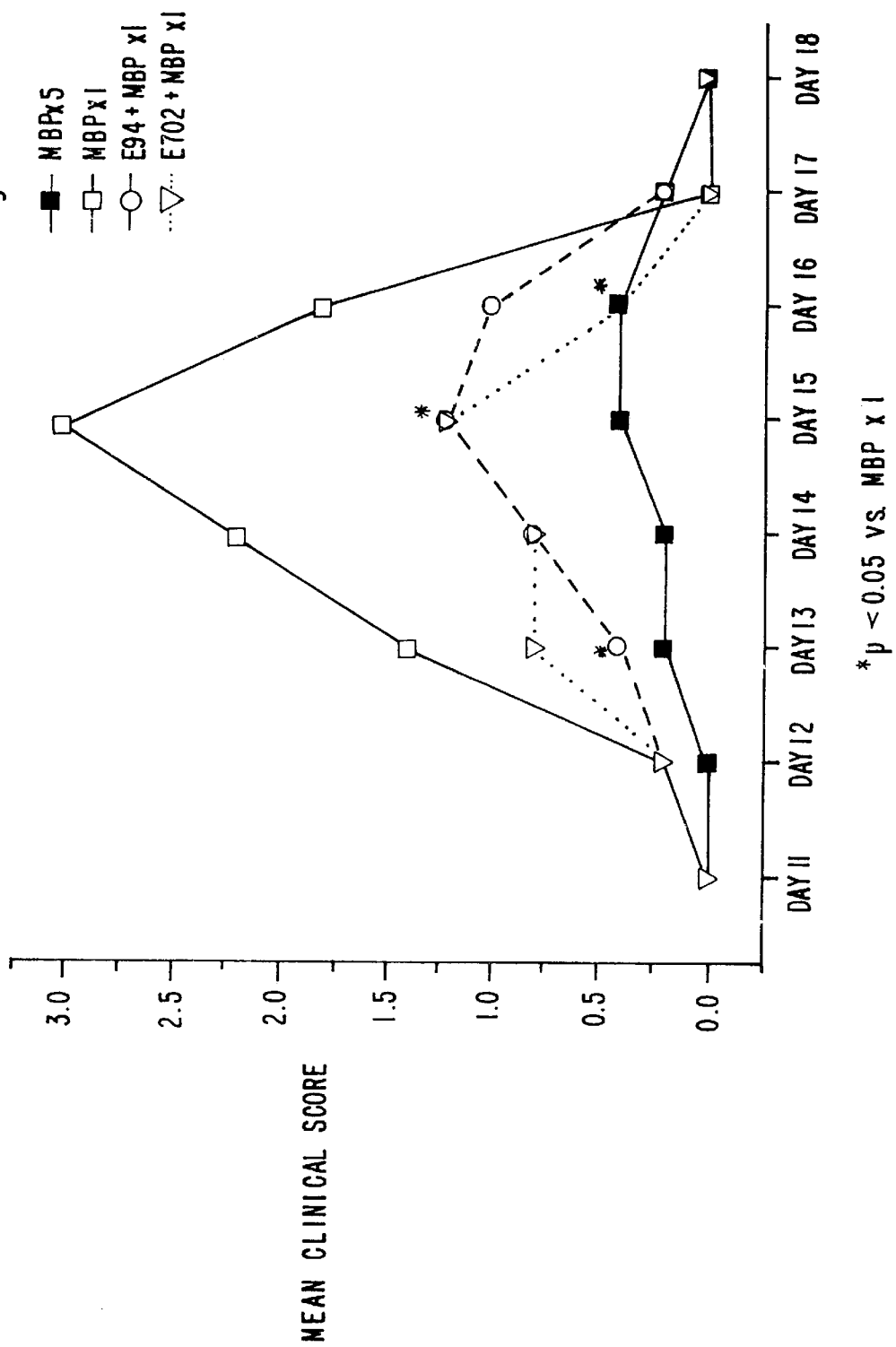
FIG. 10 is a graphic representation of the Mean Clinical Score for the progression of EAE over time in Lewis rats fed a single dose of MPB with N-salicyloyl phenylalanine (E94) or 3-[4-(N-2,3-dimethoxybenzoyl)]aminophenyl propionic acid (E702) derivatized amino acid delivery agents; MBP alone in 1 dose; or MBP given in 5 doses in accordance with Example 11.
Figure 11:
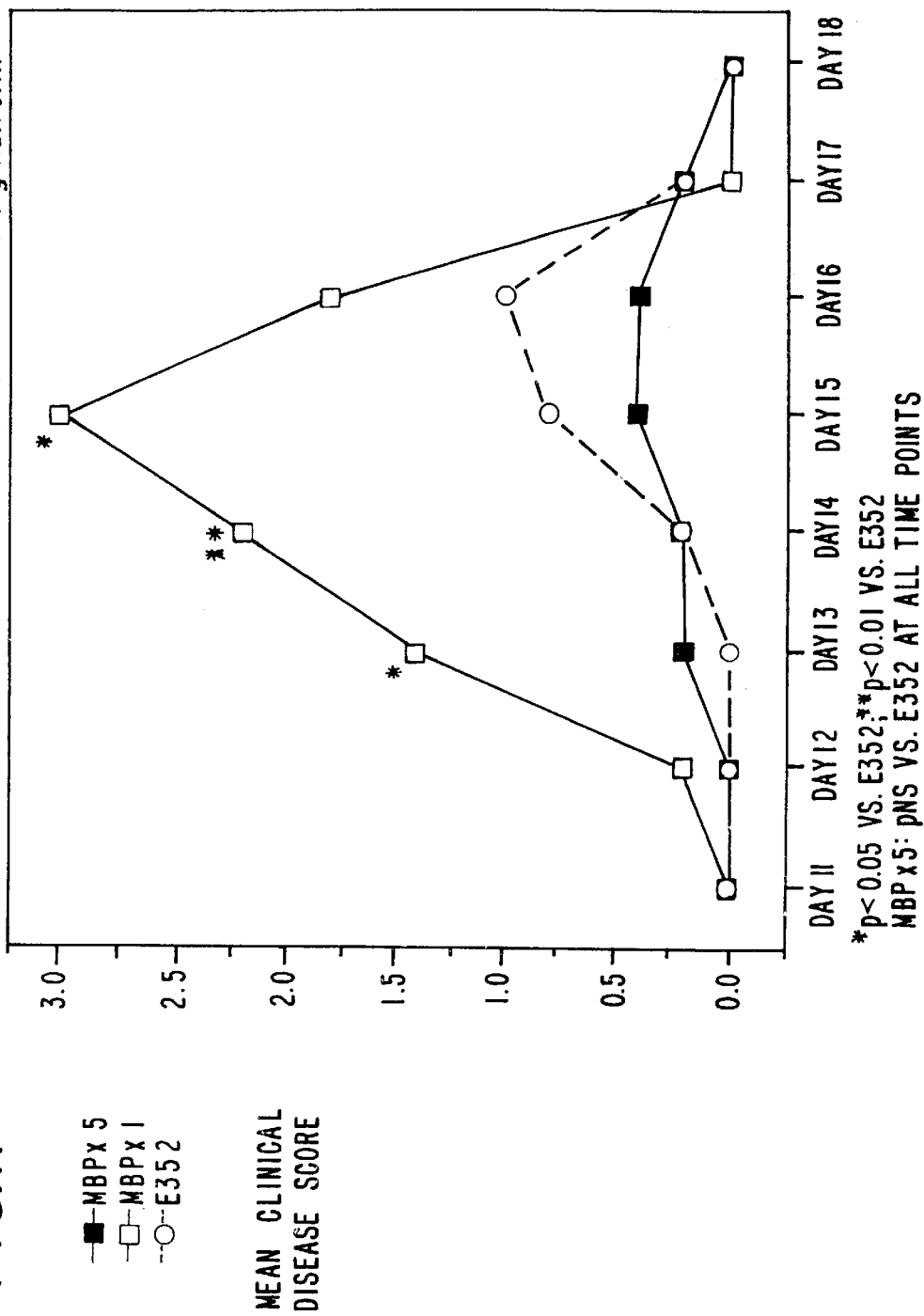
FIG. 11 is a graphic representation of the Mean Clinical Score for the progression of EAE over time in Lewis rats fed a single dose of MPB with 4-[4-(N-salicyloyl)]aminophenyl butyric acid (E352) derivatized amino acid delivery agent; MBP alone in 1 dose; or MBP given in 5 doses in accordance with Example 11.

FIGS. 10 and 11 show the suppression of clinical disease by a single dose of MPB with E94 and E702 (FIG. 10) and E352 (FIG. 11). The presence of delivery agents suppressed disease symptoms to a degree statistically identical to 5 doses of MBP alone, and significantly more than a single dose of MBP alone at the time points indicated. In addition, the mean day of onset of paralysis (defined as a clinical disease score less than or equal to 1) was delayed from Day 13 after a single dose of MBP alone to Day 15 in the presence of E94 or E702 and Day 16 in the presence of E352.

Figure 12:
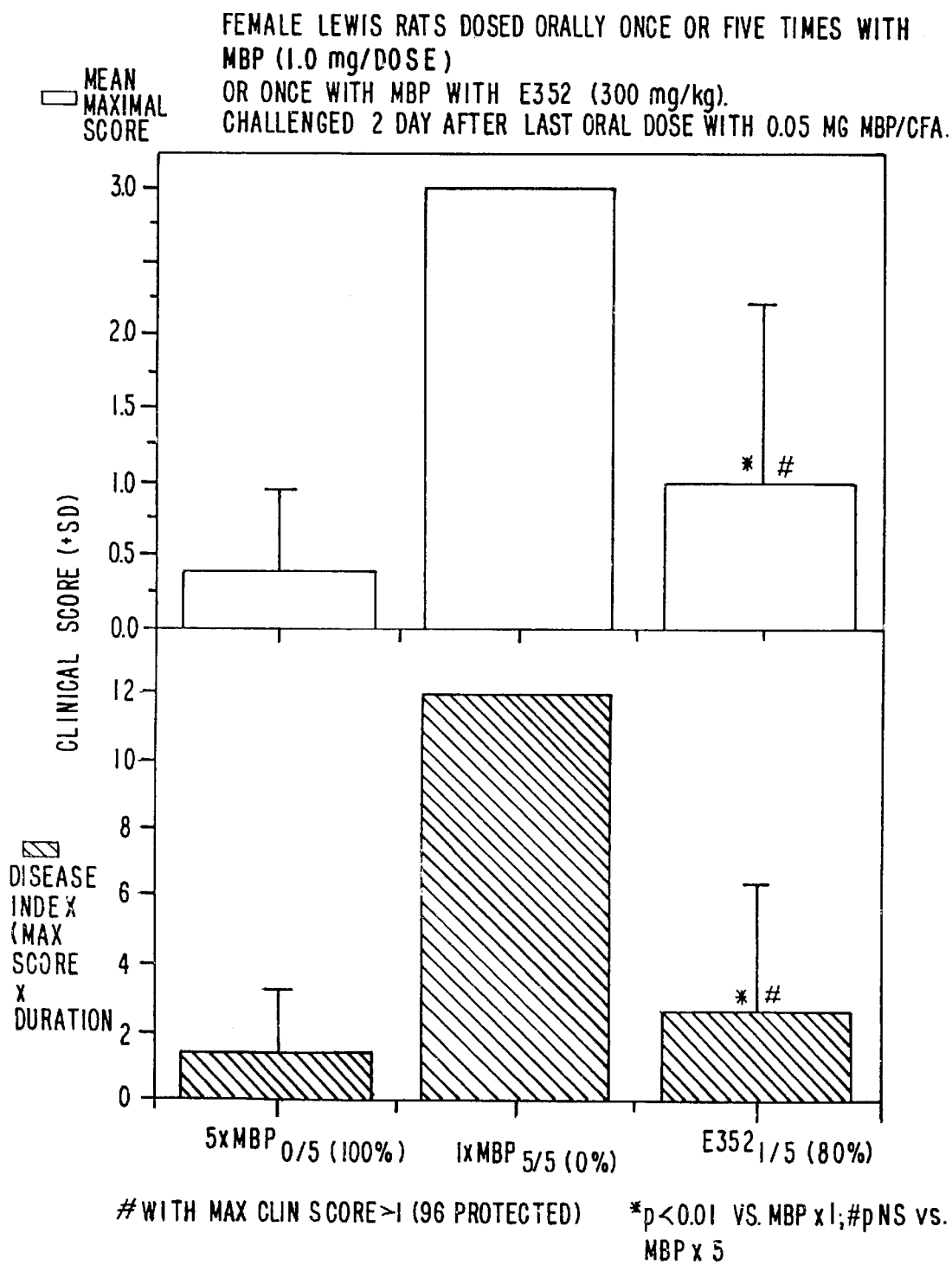
FIG. 12 is a graphic representation of the mean Maximal Score per group and the Mean Disease Index per group (defined as the highest mean score multiplied by the duration of symptoms) for Lewis rats dosed with a single dose of MBP and with 4-[4-(N-salicyloyl)]aminophenyl butyric acid (E352) derivatized amino acid delivery agent; MBP alone in 1 dose; or MBP given in 5 doses in accordance with Example 11. The subscripts in the group labels refer to the number of paralyzed rats in each group, and the "% protection", i.e. the percent of animals that were not paralyzed.

FIG. 12 shows the mean Maximal Score per group and the Mean Disease Index per group (defined as the highest mean score multiplied by the duration of symptoms) for rats dosed with a single dose of MBP and E352 vs. one or five doses of MBP alone. In both cases, the presence of E352 suppressed these disease parameters significantly compared with the dose of MBP alone, and was statistically identical to the five-dose MBP group.

The subscripts in the group labels refer to the number of paralyzed rats in each group, and the "% protection", i.e. the percent of animals that were not paralyzed.

We claim:

1. A method of inducing oral tolerance in an animal, comprising orally administering to said animal a pharmaceutical formulation comprising an antigen and a delivery agent comprising at least one derivatized amino acid or a salt thereof in an amount sufficient to induce tolerance to said antigen.

2. The method of claim 1, wherein the derivatized amino acid is an acylated amino acid compound of the formula

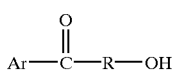 (I)

wherein:
Ar is a substituted or unsubstituted phenyl,

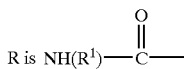

$R^1$ is $C_1$ to $C_{10}$ alkyl, $C_1$ to $C_{10}$ alkenyl, phenyl, naphthyl, ($C_1$ to $C_{10}$ alkyl)phenyl, ($C_1$ to $C_{10}$ alkenyl)phenyl, ($C_1$ to $C_{10}$ alkyl)naphthyl, ($C_1$ to $C_{10}$ alkenyl)naphthyl;

$R^1$ is optionally substituted with $C_1$ to $C_4$ alkyl, $C_1$ to $C_4$ alkenyl, $C_1$ to $C_4$ alkoxy, —OH, —SH and —$CO_2R^2$, cycloalkyl, cycloalkenyl, heteroalkyl, alkaryl, heteroaryl, heteroalkaryl, or any combination thereof; and $R^2$ is hydrogen, $C_1$ to $C_4$ alkyl or $C_1$ to $C_4$ alkenyl.

3. The method of claim 1, wherein the derivatized amino acid is a sulphonated amino acid compound of the formula Ar—SO$_2$—(R)—OH     (II)

wherein:
Ar is a substituted or unsubstituted phenyl,

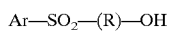

$R^1$ is $C_1$ to $C_{10}$ alkyl, $C_1$ to $C_{10}$ alkenyl, phenyl, naphthyl, ($C_1$ to $C_{10}$ alkyl)phenyl, ($C_1$ to $C_{10}$ alkenyl)phenyl, ($C_1$ to $C_{10}$ alkyl)naphthyl, ($C_1$ to $C_{10}$ alkenyl)naphthyl;

$R^1$ is optionally substituted with $C_1$ to $C_4$ alkyl, $C_1$ to $C_4$ alkenyl, $C_1$ to $C_4$ alkoxy, —OH, —SH and —$CO_2R^2$, cycloalkyl, cycloalkenyl, heteroalkyl, alkaryl, heteroaryl, heteroalkaryl, or any combination thereof; and $R^2$ is hydrogen, $C_1$ to $C_4$ alkyl or $C_1$ to $C_4$ alkenyl.

4. The method of claim 1, wherein the antigen is selected from the group consisting of synthetic proteins, naturally produced proteins, synthetic peptides, naturally produced peptides, carbohydrates and lipopolysaccharides.

5. The method of claim 1, wherein the antigen is associated with the induction of auto-immune diseases, clinical (allergic) hypersensitivities or allograft rejection, and sub-units or extracts therefrom.

6. The method of claim 1, wherein the formulation incorporates the derivatized amino acid at a dose of 100–1000 mg per kg of body weight.

7. The method of claim 6, wherein the formulation incorporates the derivatized amino acid at a dose of 250–750 mg per kg of body weight.

8. The method of claim 1, wherein the formulation additionally incorporates an enzyme inhibitor.

9. The method of claim 1, wherein the formulation additionally incorporates an adjuvant.

10. A pharmaceutical formulation for inducing oral tolerance in a mammal, comprising an antigen and a delivery agent comprising at least one derivatized amino acid or a salt thereof in an amount sufficient to induce oral tolerance.

11. The pharmaceutical formulation of claim 10, wherein the derivatized amino acid is an acylated amino acid compound of the formula

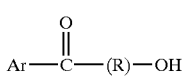 I wherein:
Ar is a substituted or unsubstituted phenyl

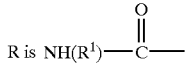

$R^1$ is $C_1$ to $C_{10}$ alkyl, $C_1$ to $C_{10}$ alkenyl, phenyl, naphthyl, ($C_1$ to $C_{10}$ alkyl)phenyl, ($C_1$ to $C_{10}$ alkenyl)phenyl, ($C_1$ to $C_{10}$ alkyl)napthyl, ($C_1$ to $C_{10}$ alkenyl)naphthyl;

$R^1$ is optionally substituted with $C_1$ to $C_4$ alkyl, $C_1$ to $C_4$ alkenyl,$C_1$ to $C_4$ alkoxy, —OH, —SH and —$CO_2R^2$, cycloalkyl, cycloalkenyl, heteroalkyl, alkaryl, heteroaryl, heteroalkaryl, or any combination thereof; and $R^2$ is hydrogen, $C_1$ to $C_4$ alkyl or $C_1$ to $C_4$ alkenyl.

12. The pharmaceutical formulation of claim 10, wherein the derivatized amino acid is a sulphonated amino acid compound of the formula Ar—SO$_2$—(R)—OH     II wherein:
Ar is a substituted or unsubstituted phenyl

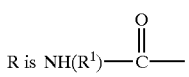

$R^1$ is $C_1$ to $C_{10}$ alkyl, $C_1$ to $C_{10}$ alkenyl, phenyl, naphthyl, ($C_1$ to $C_{10}$ alkyl)phenyl, ($C_1$ to $C_{10}$ alkenyl)phenyl, ($C_1$ to $C_{10}$ alkyl)naphthyl, ($C_1$ to $C_{10}$ , alkenyl)naphthyl;

$R^1$ is optionally substituted with $C_1$ to $C_4$ alkyl, $C_1$ to $C_4$ alkenyl,$C_1$ to $C_4$ alkoxy, —OH, —SH and —$CO_2R^2$, cycloalkyl, cycloalkenyl, heteroalkyl, alkaryl, heteroaryl, heteroalkaryl, or any combination thereof; and $R^2$ is hydrogen, $C_1$ to $C_4$ alkyl or $C_1$ to $C_4$ alkenyl.

13. The pharmaceutical formulation claim 10, wherein the derivatized amino acid is administered at a dose of about 100–1000 mg per kg of body weight.

14. The pharmaceutical formulation claim 10, wherein the derivatized amino acid is administered at a dose of about 250–750 mg per kg of body weight.

15. The pharmaceutical formulation of claim 10, wherein the antigen is selected from the group consisting of synthetic proteins, naturally produced proteins, synthetic peptides, naturally produced peptides, carbohydrates and lipopolysaccharides.

16. The pharmaceutical formulation of claim 10, wherein the antigen is associated with the induction of auto-immune diseases, clinical (allergic) hypersensitivities or allograft rejection, and subunits or extracts therefrom.

17. The pharmaceutical formulation of claim 10, wherein the formulation additionally incorporates an adjuvant.

18. The pharmaceutical formulation of claim 10, wherein the formulation additionally incorporates an enzyme inhibitor.

19. The method of claim 2, wherein the derivatized amino acid is an acylated amino acid compound of the formula

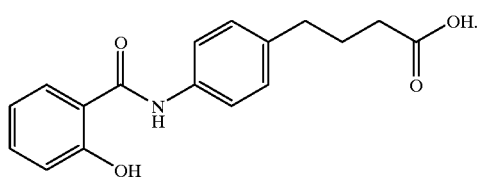

20. The method of claim 2, wherein the derivatized amino acid is an acylated amino acid compound of the formula

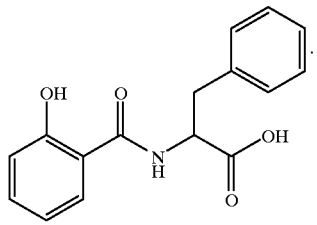

21. The method of claim 2, wherein the derivatized amino acid is an acylated amino acid compound of the formula

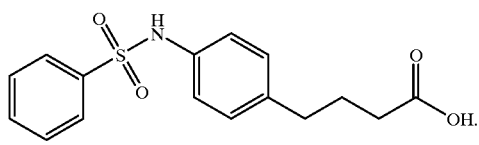

22. The method of claim 2, wherein the derivatized amino acid is an acylated amino acid compound of the formula

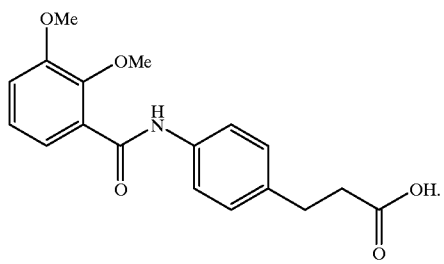

23. The method of claim 2, wherein the derivatized amino acid is an acylated amino acid compound of the formula

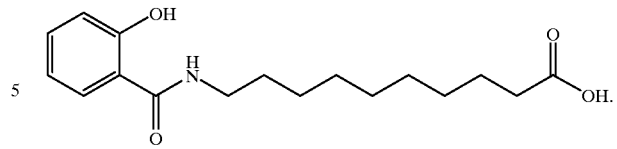

24. The method of claim 2, wherein the derivatized amino acid is an acylated amino acid compound of the formula

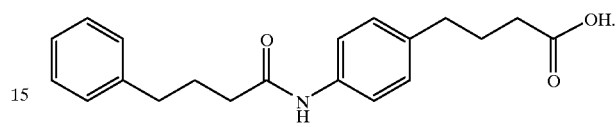

25. The method of claim 2, wherein the derivatized amino acid is an acylated amino acid compound of the formula

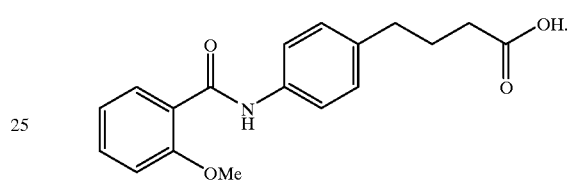

26. The method of claim 2, wherein the derivatized amino acid is an acylated amino acid compound of the formula

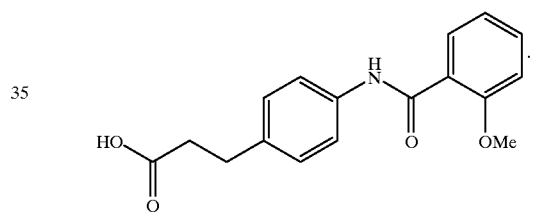

27. The method of claim 2, wherein the derivatized amino acid is an acylated amino acid compound of the formula

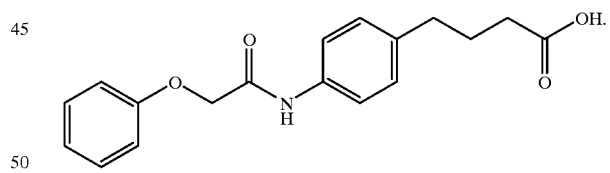

* * * * *